United States Patent
Hight et al.

(10) Patent No.: US 9,968,502 B2
(45) Date of Patent: May 15, 2018

(54) SYSTEM AND PROCESS OF LOCATING A MEDICAL IMAGING DEVICE

(71) Applicant: Allen Medical Systems, Inc., Batesville, IN (US)

(72) Inventors: Joshua C. Hight, Somerville, MA (US); Jesse Scott Drake, Westborough, MA (US); Varad Narayan Srivastava, Loveland, OH (US); David Lance Ribble, Indianapolis, IN (US)

(73) Assignee: Allen Medical Systems, Inc., Batesville, IN (US)

( * ) Notice: Subject to any disclaimer, the term of this patent is extended or adjusted under 35 U.S.C. 154(b) by 0 days. days.

(21) Appl. No.: 15/198,522

(22) Filed: Jun. 30, 2016

(65) Prior Publication Data
US 2017/0000675 A1    Jan. 5, 2017

Related U.S. Application Data

(60) Provisional application No. 62/187,093, filed on Jun. 30, 2015.

(51) Int. Cl.
*G01B 11/14*      (2006.01)
*A61G 13/02*      (2006.01)
*A61B 6/04*       (2006.01)

(52) U.S. Cl.
CPC .............. *A61G 13/02* (2013.01); *A61B 6/04* (2013.01); *G01B 11/14* (2013.01); *A61G 2203/30* (2013.01); *A61G 2210/50* (2013.01)

(58) Field of Classification Search
CPC .................. G01B 11/14; A61G 13/02
USPC .................................. 356/614, 620
See application file for complete search history.

(56) References Cited

U.S. PATENT DOCUMENTS

| | | | |
|---|---|---|---|
| 5,446,548 A * | 8/1995 | Gerig | A61B 6/08 250/462.1 |
| 6,947,786 B2 * | 9/2005 | Simon | A61B 6/12 600/424 |
| 7,075,661 B2 * | 7/2006 | Petty | G01S 5/163 356/603 |
| 8,675,911 B2 * | 3/2014 | Barbier | G01S 5/163 348/169 |
| 9,649,168 B2 * | 5/2017 | Rahimian | A61B 90/11 |

(Continued)

*Primary Examiner* — Roy M Punnoose
(74) *Attorney, Agent, or Firm* — Dinsmore & Shohl LLP

(57) ABSTRACT

Systems and processes of locating a medical imaging device relative to a person support apparatus and/or a patient are provided. An example system includes an optical sensor disposed at the person support apparatus and/or the imaging device. In embodiments, optical markers may also be disposed on one or more of the medical imaging device, the person support apparatus and/or patient for determining the relative location of the imaging device and the person support apparatus and/or patient. In other embodiments, an optical sensor may use image recognition processes to determine the relative locations. By locating and positioning the medical imaging device without taking recursive medical images to position the device, the imaging device can be positioned for a subsequent image without exposing the patient and healthcare professionals to additional radiation generated while positioning the medical imaging device, thereby reducing risk to the patient and the medical staff.

26 Claims, 17 Drawing Sheets

(56) References Cited

U.S. PATENT DOCUMENTS

2006/0028656 A1* 2/2006 Venkatesh ............... G01J 3/10
356/620
2013/0085510 A1* 4/2013 Stefanchik .......... G06F 19/3481
606/130

* cited by examiner

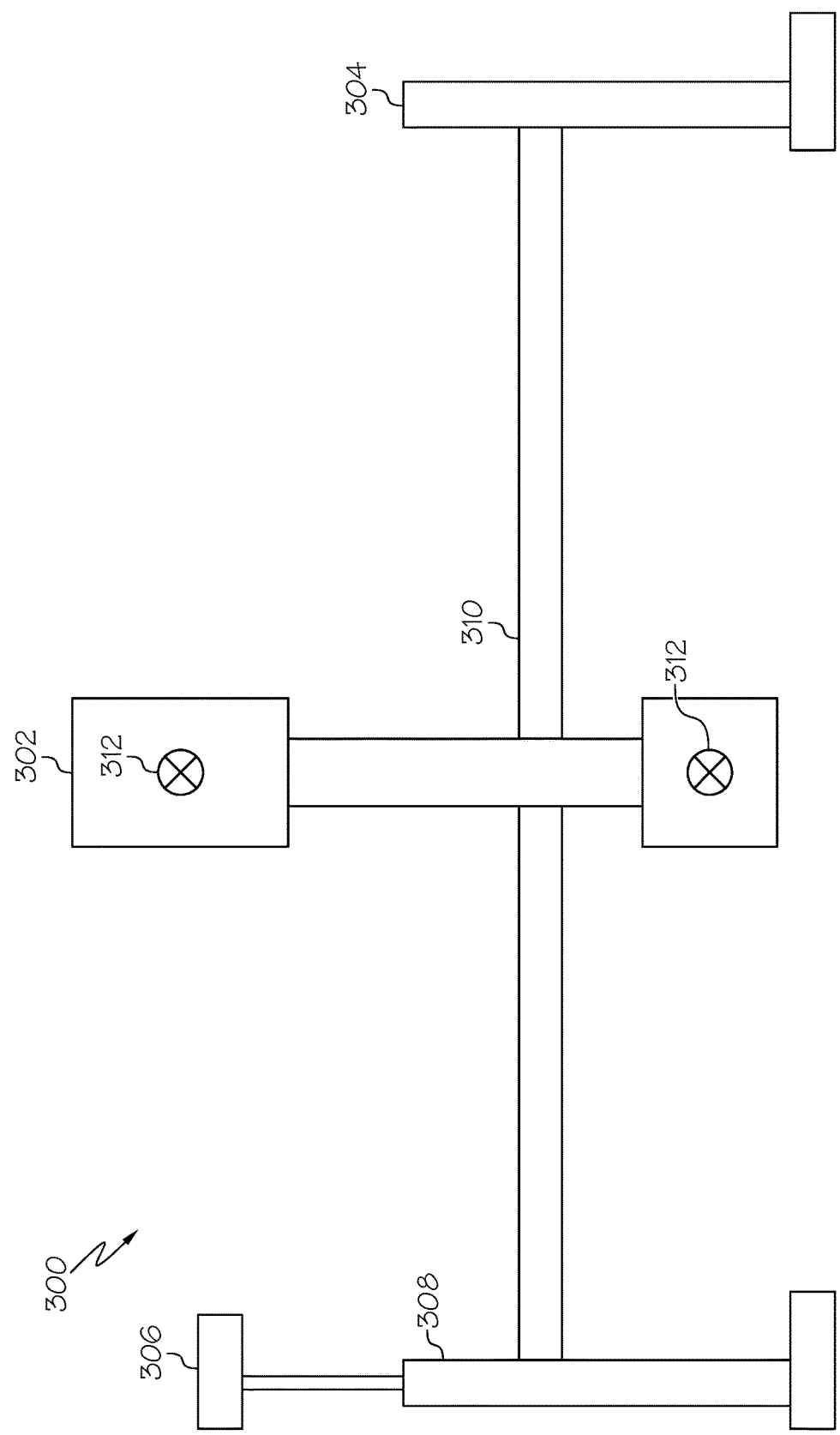

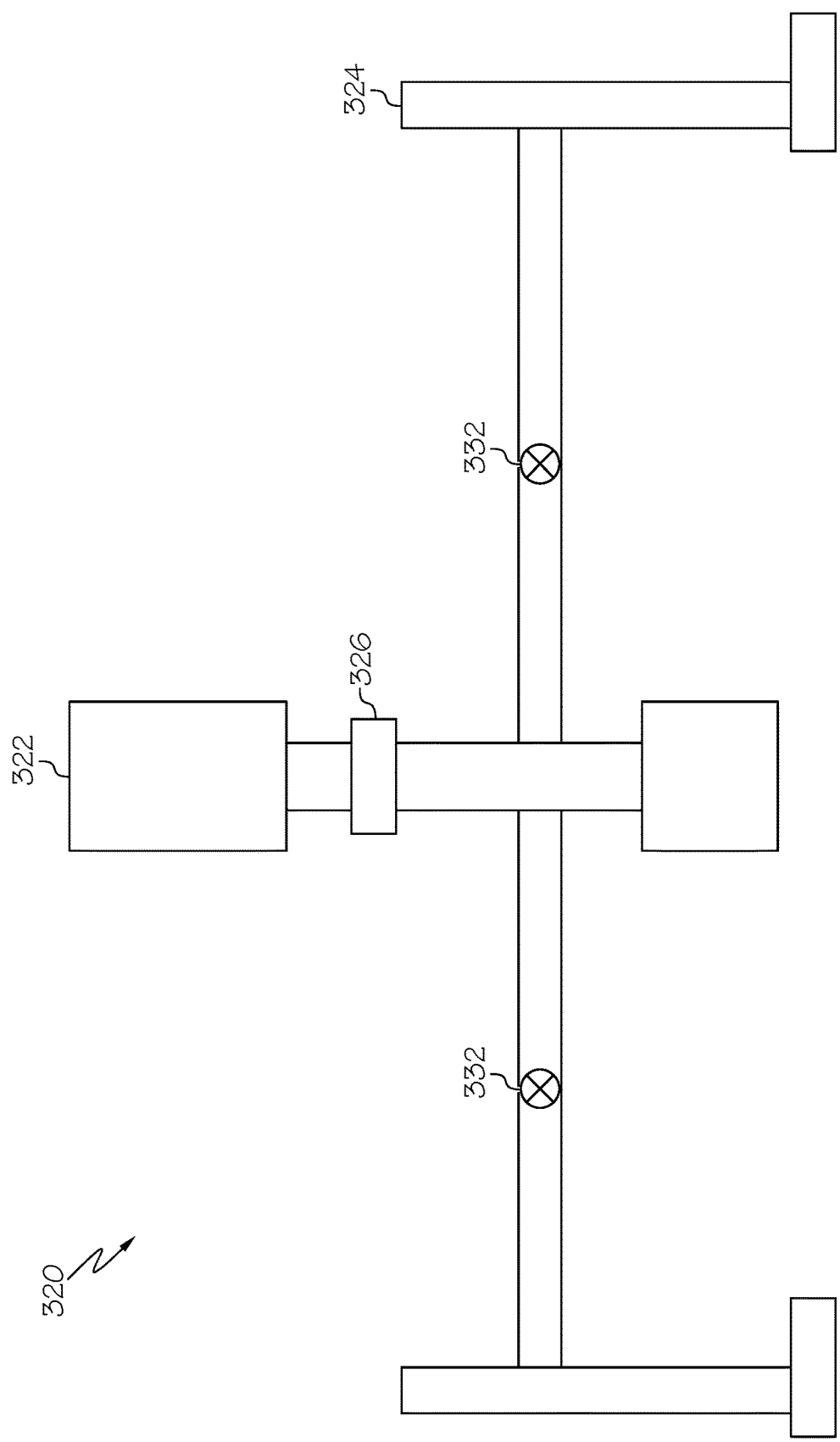

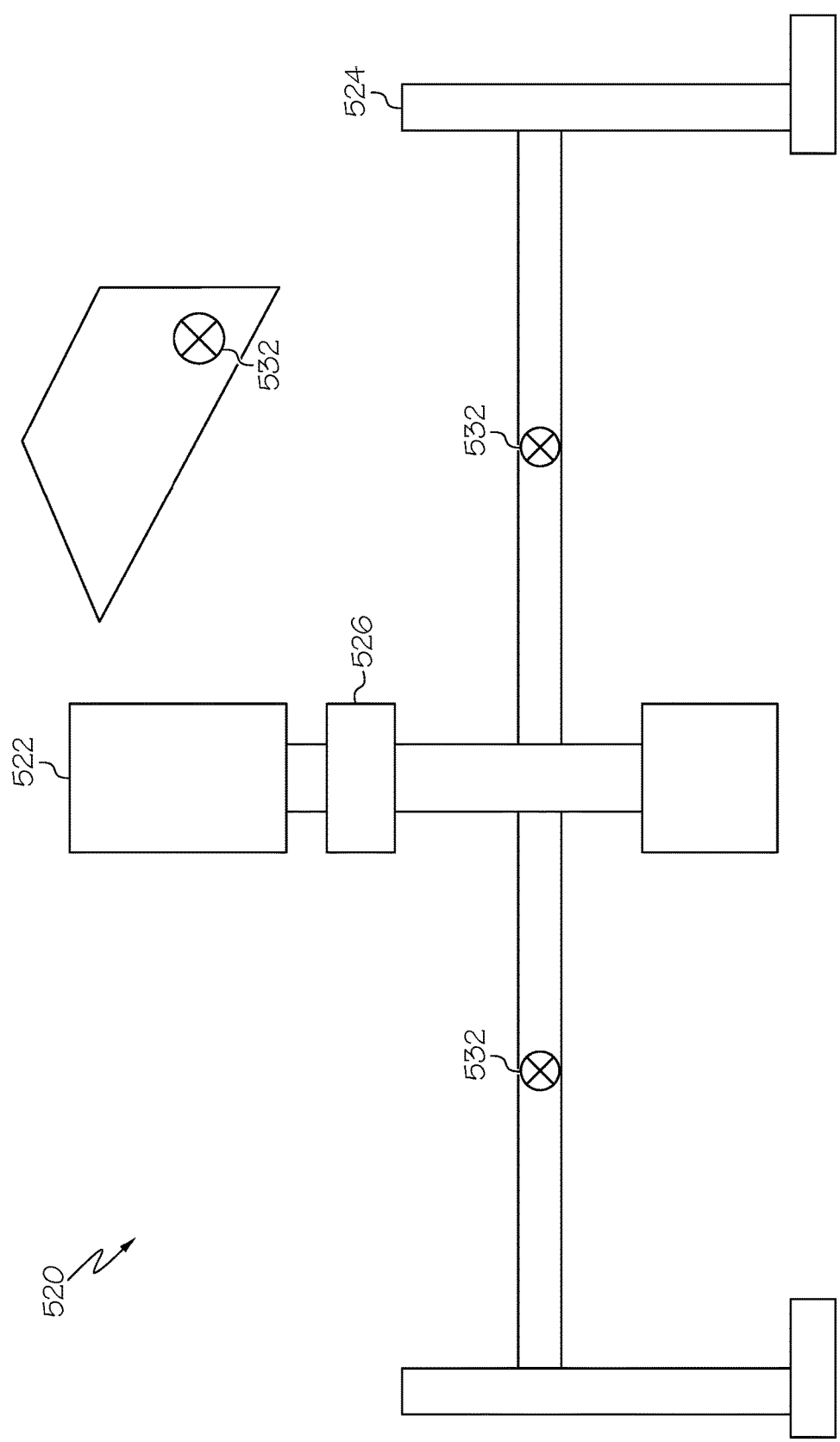

SYSTEM AND PROCESS OF LOCATING A MEDICAL IMAGING DEVICE

CROSS-REFERENCE TO RELATED APPLICATIONS

This application claims the benefit of U.S. provisional application No. 62/187,093, filed 30 Jun. 2015, which is hereby incorporated by reference as though fully set forth herein.

BACKGROUND

Field

The present specification generally relates to systems and processes for locating imaging devices and, more specifically, to systems and processes for optical location of medical imaging devices.

Technical Background

In some surgical and diagnostic procedures, it may be useful to locate an imaging device in a precise location to take an image of a patient. Where an initial image is taken prior to or during surgery, for example, a surgeon may want to take a later image during or after surgery to compare to the initial image. When a patient and/or the imaging device has been moved relative to each other, the imaging device may be positioned in the same location relative to the patient to take the subsequent image that may be compared to the initial image or may be used to locate a region of interest on the patient for the surgeon.

Accordingly, a need exists for locating an imaging device relative to a patient and/or to a person support apparatus adapted to support a patient during a medical procedure.

SUMMARY

In one implementation, a system of locating a medical imaging device relative to a person support apparatus or a patient is provided. The system includes a person support apparatus adapted to support a patient and a medical imaging device adapted to capture an image of the patient on the person support apparatus. An optical sensor includes a light sensor communicatively coupled to a processor. The optical sensor is adapted to receive a light signal corresponding to at least one of the person support apparatus and the medical imaging device, the processor adapted to receive a signal corresponding to the light signal from the light sensor and determine a position of at least one of the person support apparatus, the medical imaging device and the patient based upon the signal.

In another implementation, a system of locating a medical imaging device relative to a person support apparatus or a patient is provided. The system includes a person support apparatus adapted to support a patient and a medical imaging device adapted to capture an image of the patient on the person support apparatus. An optical sensor includes a light sensor communicatively coupled to a processor. The optical sensor disposed on at least one of the person support apparatus and the medical imaging device and adapted to receive a light signal corresponding to the other one of the person support apparatus and the medical imaging device, the processor adapted to receive a signal corresponding to the light signal from the light sensor and determine a position of the other one of the person support apparatus and the medical imaging device based upon the signal.

In yet another implementation, a process of locating a medical imaging device relative to a person support apparatus or a patient is provided. The process includes capturing a light signal at a light sensor of an optical sensor. The light signal corresponds to at least one of a patient, a person support apparatus adapted to support a patient and a medical imaging device. In some embodiments, the optical sensor is disposed on the patient, the person support apparatus, the medical imaging device or any other device, component, structure or feature adjacent to or nearby a surgical, diagnostic or treatment area. For example, the sensor may be connected to or disposed nearby any device, component, structure and/or feature in a surgical room, such as but not limited to the surgical light, an anesthesia machine, a monitor, a table, a shelf, a wall, a ceiling, a floor, a post, a beam or other device, component, structure and/or feature. The process also includes receiving an electrical signal from the light sensor corresponding to the light signal at a processor of the optical sensor. The process further determines a relative location of at least two of the medical imaging device, the person support apparatus and the patient based on the electrical signal using the processor.

In another implementation, a process of locating a medical imaging device relative to a person support apparatus or a patient is provided. The process includes capturing a light signal at a light sensor of an optical sensor. The light signal corresponds to at least one of a patient, a person support apparatus adapted to support a patient and a medical imaging device. The optical sensor is disposed on at least one of the patient, the person support apparatus and the medical imaging device. The process also includes receiving an electrical signal from the light sensor corresponding to the light signal at a processor of the optical sensor. The process further determines a relative location of the medical imaging device and the person support apparatus based on the electrical signal using the processor.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 6A schematically depicts an example system including a medical imaging device and a person support apparatus according to one or more embodiments shown or described herein;

FIG. 6B schematically depicts an example system including a medical imaging device and a person support apparatus according to one or more embodiments shown or described herein;

FIG. 7B schematically depicts an example system including a medical imaging device, a person support apparatus and a surgical light according to one or more embodiments shown or described herein;

DETAILED DESCRIPTION

Systems and processes of locating a medical imaging device, such as a radiographic, fluoroscopy, mammography, computed tomography, magnetic resonance imaging or other medical imaging device, relative to a person support apparatus and/or a patient are provided. An example system includes an optical sensor disposed at the person support apparatus and/or the imaging device. In embodiments, optical markers may also be disposed on one or more of the medical imaging device, the person support apparatus and/or patient for determining the relative location of the imaging device and the person support apparatus and/or patient. In other embodiments, an optical sensor may use image recognition processes to determine the relative locations. By locating and positioning the medical imaging device without taking recursive medical images to position the device, the imaging device can be positioned for a subsequent image without exposing the patient and healthcare professionals to additional radiation generated while positioning the medical imaging device, thereby reducing risk to the patient and the medical staff.

Figure 1A:
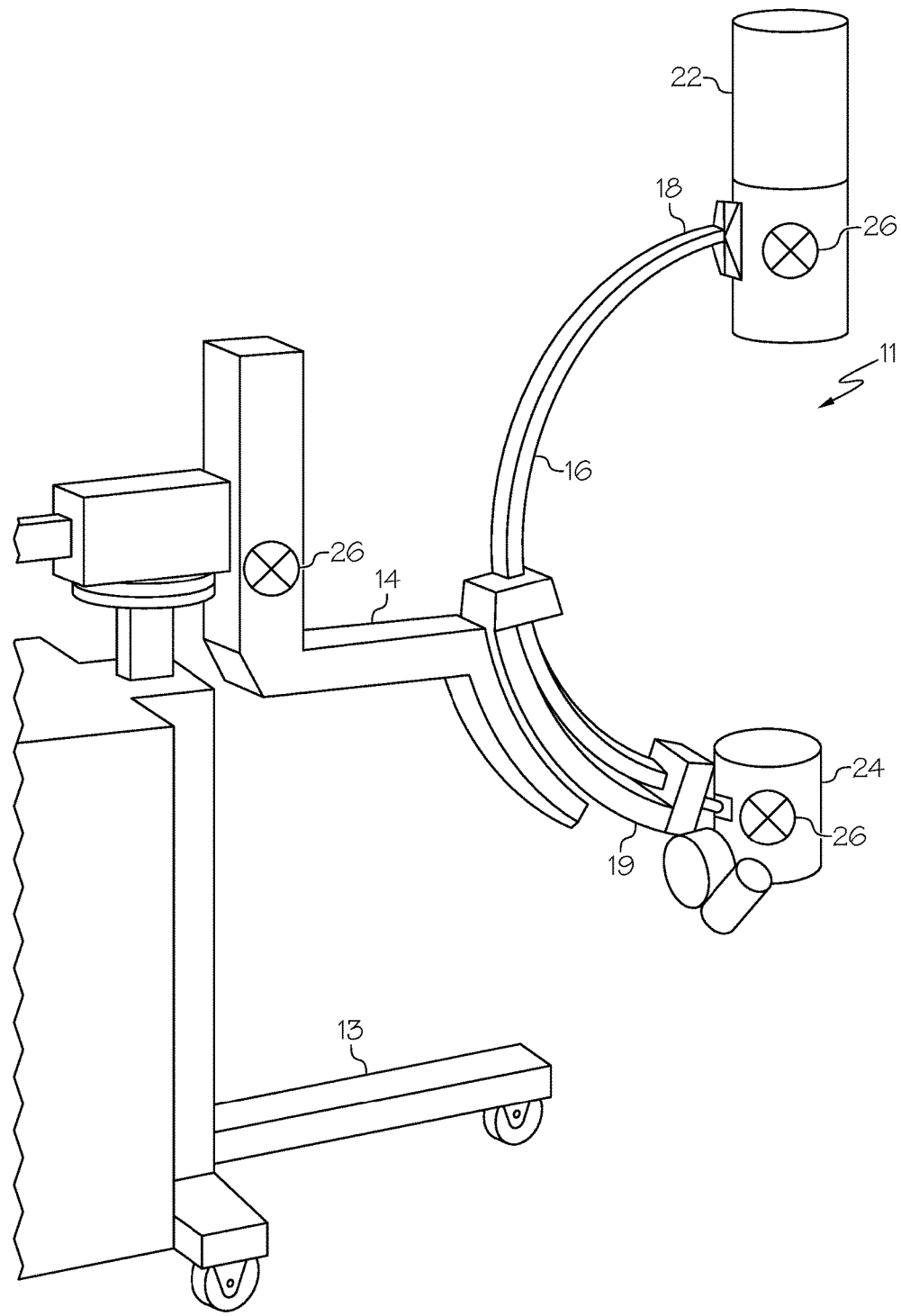
FIG. 1A schematically depicts an example medical imaging device for use in a system for monitoring an imaging device according to one or more embodiments shown herein.
Figure 1B:
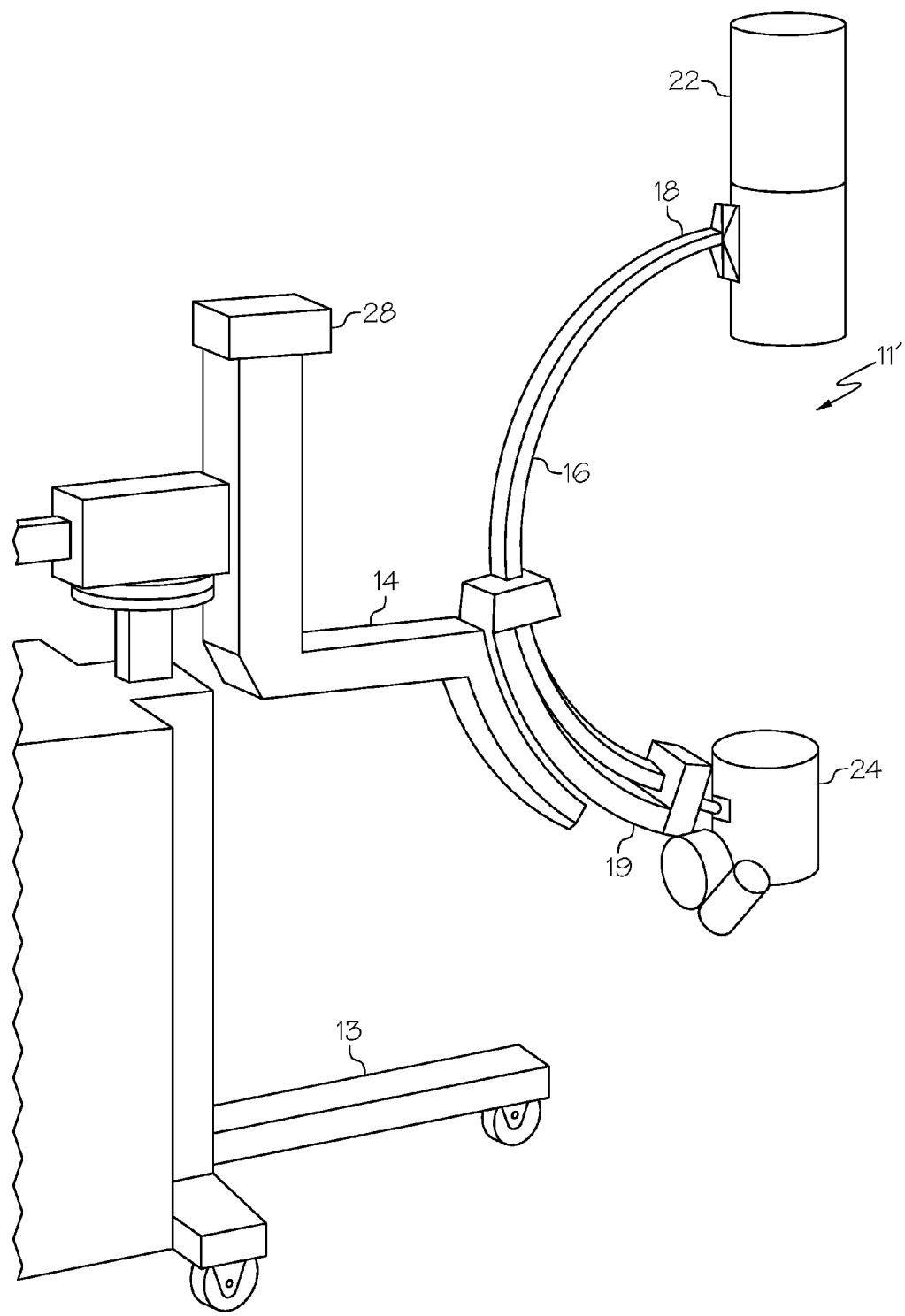
FIG. 1B schematically depicts another example medical imaging device for use in a system for monitoring an imaging device according to one or more embodiments shown herein.

FIGS. 1A and 1B depict example medical imaging devices that may be used within a method and system for optical location of the imaging device. In the particular implementations of FIGS. 1A and 1B, for example, the medical imaging device 11 includes an operating room C-arm radiographic imaging device 11. Although a C-arm radiographic imaging device is shown, other imaging devices, such as other X-ray configurations, fluoroscopic imaging devices, mammography imaging devices, computed tomography (CT) imaging devices, magnetic resonance imaging (MRI) devices or other medical imaging devices may also be used. In FIGS. 1A and 1B, the same reference numerals are used throughout the drawings to refer to the same or like parts.

Referring to FIG. 1A, the C-arm radiographic imaging device 11, in this implementation, has a mobile base 13, an outwardly extending support 14, and a C-arm 16. The C-arm 16 generally resembles the shape of the letter C, but may have any arcuate shape. The C-arm 16 has first 18 and second 20 ends positioned opposite each other. An imaging source 22 is positioned on the first end 18 and an image receiver and/or intensifier 24 is positioned on the second end 19. In this arrangement, the receiver and/or intensifier 24 is positioned directly opposite the imaging source 22. As shown in FIG. 1A, the imaging source 22 is typically positioned on the first 18, or upper, end with the receiver and/or intensifier 24 positioned on the second 19, or lower, end. In this configuration, the x-ray source 22 directs radiographic rays (e.g., x-rays) downward toward the patient during an imaging procedure. Of course, the imaging source 22 and receiver and/or intensifier 24 can be reversed in position.

In the embodiment shown in FIG. 1A, the imaging device 11 further includes optical markers 26 disposed on one or more surfaces of the imaging device 11. As discussed in more detail below, the optical markers may be detected by an optical sensor to determine a location of the imaging device 11 relative to the optical sensor, which may be disposed on or fixed relative to a person support apparatus, such as a surgical table, cart, gurney, cot or the like. Of course, the optical markers may be disposed on the person support apparatus and/or patient and the optical sensor may be disposed on the imaging device and still be adapted to determine a position of the imaging device 11 relative to the person support apparatus.

Referring to FIG. 1B, the C-arm radiographic imaging device 11', in this implementation, has a mobile base 13, an outwardly extending support 14, and a C-arm 16. The C-arm 16 generally resembles the shape of the letter C, but may have any arcuate shape. The C-arm 16 has first 18 and second 19 ends positioned opposite each other. An imaging source 22 is positioned on the first end 18 and an image receiver and/or intensifier 24 is positioned on the second end 19. In this arrangement, the receiver and/or intensifier 24 is positioned directly opposite the imaging source 22. As shown in FIG. 1B, the imaging source 22 is typically positioned on the first 18, or upper, end with the receiver and/or intensifier 24 positioned on the second 19, or lower, end. In this configuration, the x-ray source 22 directs radiographic rays (e.g., x-rays) downward toward the patient during an imaging procedure. Of course, the imaging source 22 and receiver and/or intensifier 24 can be reversed in position.

In the embodiment shown in FIG. 1B, the imaging device 11' further includes an optical sensor 28 disposed on one or more surfaces of the imaging device 11'. As discussed in more detail below, the optical sensor may detect optical markers disposed on a person support apparatus and/or a patient to determine a location of the imaging device 11' relative to the optical sensor, which may be disposed on or fixed relative to a person support apparatus, such as a surgical table, cart, gurney, cot or the like, and/or the patient.

Figure 2A:
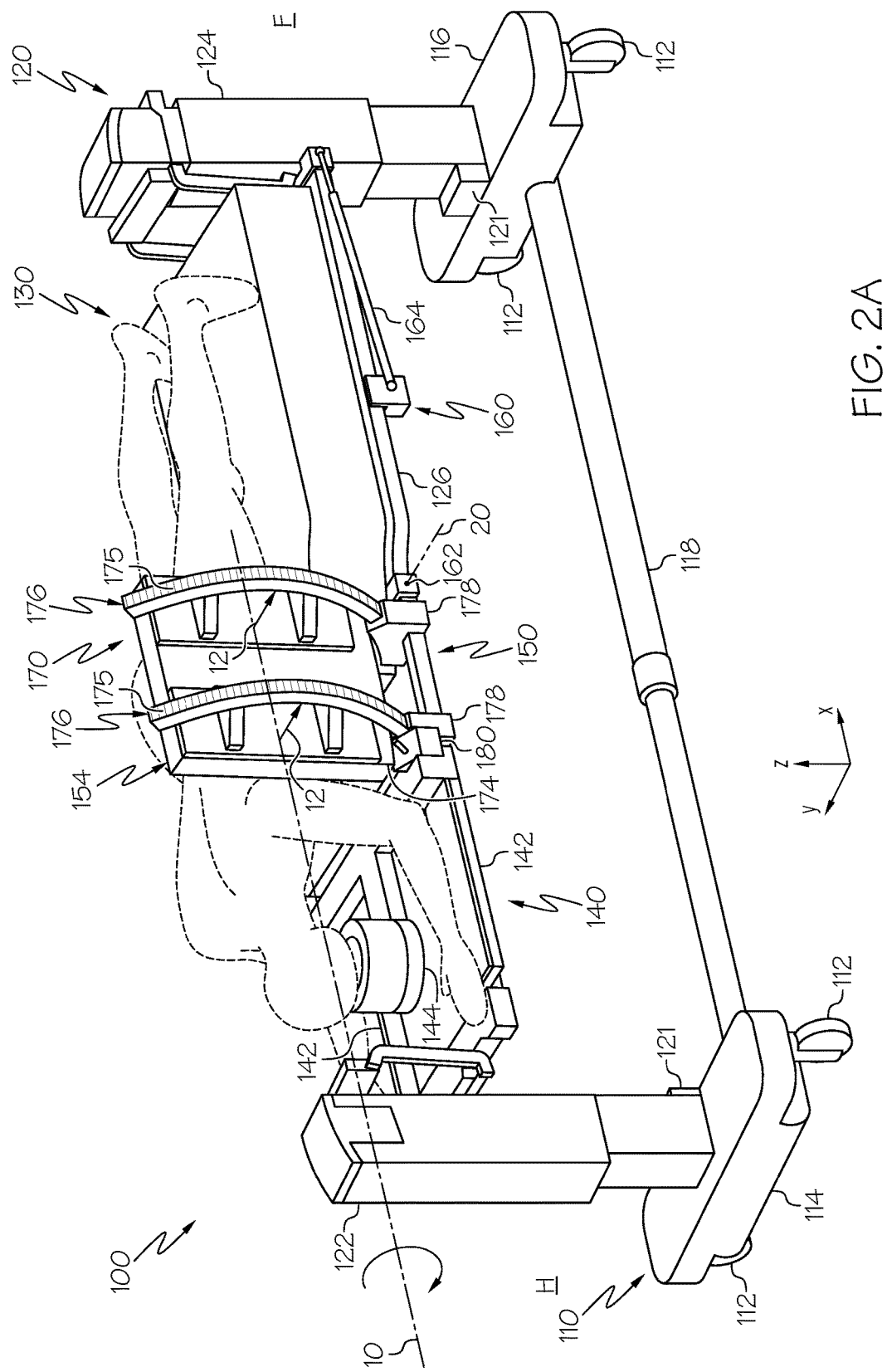
FIG. 2A schematically depicts a perspective view of a person support apparatus including a person repositioning assembly according to one or more embodiments shown or described herein.

Example implementations of person support apparatuses are illustrated in FIGS. 2A through 5 of the accompanying drawings. The person support apparatuses may be used, for example, in conjunction with the methods and systems for locating a medical imaging device described herein. The same reference numerals are generally used throughout the drawings to refer to the same or like parts. One embodiment of a person support apparatus is depicted in FIG. 2A, in which the person support apparatus includes a base frame and a primary support frame supported on the base frame, where the primary support frame extends in a longitudinal direction. The person support apparatus further includes a support deck coupled to the primary support frame, the support deck including an upper segment positioned at a head end of the person support apparatus, a leg segment positioned at a foot end of the person support apparatus, and a torso segment positioned between the upper segment and the leg segment in the longitudinal direction. At least one of the upper segment, the torso segment, and the leg segment rotates with respect to the primary support frame about an axis that extends in the longitudinal direction to reposition a patient positioned on the person support apparatus. Person support apparatuses with repositioning assemblies will be described in more detail herein with specific reference to the appended drawings.

As used herein, the term "longitudinal direction" refers to the forward-rearward direction of the person support apparatus (i.e., in the +/−X-direction as depicted). The term "lateral direction" refers to the cross-direction of the person support apparatus (i.e., in the +/−Y-direction as depicted), and is transverse to the longitudinal direction. The term "vertical direction" refers to the upward-downward direction of the person support apparatus (i.e., in the +/−Z-direction as depicted), and is transverse to the lateral and the longitudinal directions. The terms "head end" and "foot end" refer to the relative location of components of the person support apparatus in the longitudinal direction.

The phrase "communicatively coupled" is used herein to describe the interconnectivity of various components of steering system and means that the components are connected either through wires, optical fibers, or wirelessly such that electrical, optical, and/or electromagnetic signals may be exchanged between the components.

Referring to FIG. 2A, a person support apparatus 100 is depicted. The person support apparatus 100 may include, for example, a two-column operating table. The person support apparatus 100 generally includes a base frame 110, a primary support frame 120 that is supported by the base frame 110, and a support deck 130 coupled to the primary support frame 120.

The base frame 110 of the person support apparatus 100 includes a forward portion 114 positioned at a head end of the person support apparatus 100 and a rearward portion 116 positioned at a foot end of the person support apparatus 100. The forward portion 114 and the rearward portion 116 are spaced apart from one another in the longitudinal direction and may be coupled to one another by a central portion 118 that extends between the forward portion 114 and the rearward portion 116 in the longitudinal direction. The central portion 118 may extendable and/or retractable in the longitudinal direction, thereby increasing or decreasing the distance between the forward portion 114 and the rearward portion 116 in the longitudinal direction. In embodiments, the forward portion 114 and the rearward portion 116 are coupled to a plurality of rollers 112, such that the person support apparatus 100 may be moved along a surface, such as a floor.

The primary support frame 120 extends upward from the base frame 110 of the person support apparatus 100. In the embodiment depicted in FIG. 2A, the primary support frame 120 includes a forward column 122 that extends upward from the forward portion 114 of the base frame 110 in the vertical direction. The primary support frame 120 further includes a rearward column 124 that extends upward from the rearward portion 116 of the base frame 110 in the vertical direction. The forward column 122 is positioned at the head end of the person support apparatus 100 and the rearward column 124 is positioned at the foot end of the person support apparatus 100, and the forward column 122 is spaced apart from the rearward column 124 in the longitudinal direction. In embodiments, the forward column 122 and the rearward column 124 are coupled to the forward portion 114 and the rearward portion 116 of the base frame 110, respectively. Alternatively, the forward column 122 and the rearward column 124 may be integral with the forward portion 114 and the rearward portion 116 of the base frame 110, respectively.

The primary support frame 120 includes a longitudinal frame 126 that is positioned above the base frame 110 in the vertical direction and that extends between the forward column 122 and the rearward column 124 in the longitudinal direction. In the embodiment depicted in FIG. 2A, the longitudinal frame 126 generally extends in the horizontal plane (i.e., the X-Y plane as depicted). In other embodiments, the longitudinal frame 126 may be contoured and may include portions that extend out of the horizontal plane. The longitudinal frame 126 supports and may be coupled to the support deck 130, which extends between the forward column 122 and the rearward column 124 in the longitudinal direction.

The forward column 122 and the rearward column 124 may be adjustable in the vertical direction such that the forward column 122 and the rearward column 124 may raise or lower the longitudinal frame 126 with respect to the base frame 110 in the vertical direction. In embodiments, at least one column actuator 121 coupled to the forward column 122 and/or the rearward column 124 and moves the forward column 122 and the rearward column 124 upward and downward in the vertical direction with respect to the base frame 110. The column actuator 121 may be a powered actuator, such as an electric motor or the like, or may be a manually powered, such as by a footpedal, a crank, or the like. The column actuator 121 include a linear actuator, such as a screw, a wheel and axle, a cam, a hydraulic actuator, a pneumatic actuator, a piezoelectric actuator, an electromechanical actuator, or the like.

Figure 5:
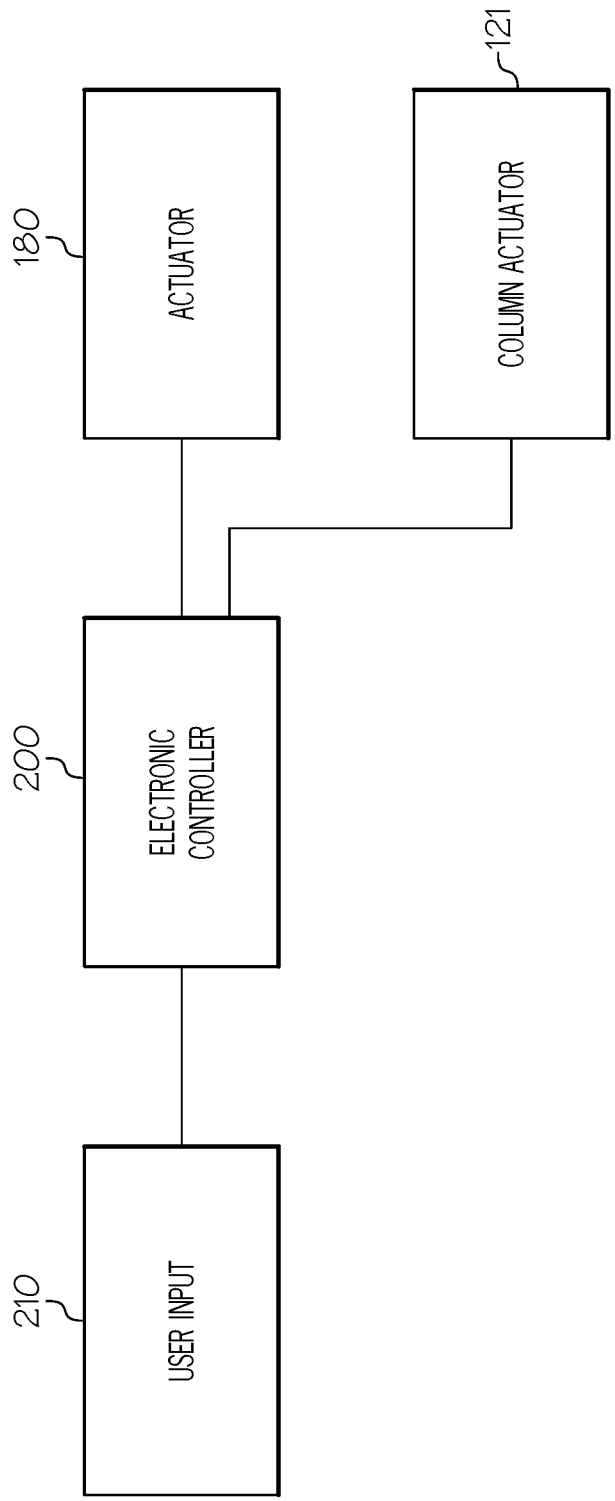
FIG. 5 schematically depicts a block diagram of a control system for the person support apparatus of FIG. 2A.

Referring to FIG. 5, in embodiments where the column actuator 121 includes an electric motor, the column actuator 121 may be communicatively coupled to an electronic controller 200. The electronic controller 200 includes a processor and a memory storing computer readable and executable instructions, which, when executed by the processor, facilitate operation of the column actuator 121. In particular, the electronic controller 200 sends a signal to the at least one column actuator 121 to raise or lower the forward column 122 and/or the rearward column 124 in the vertical direction. A user input 210 is communicatively coupled to the electronic controller 200. The user input 210 includes a device that allows a user to input various parameters into the electronic controller 200 to facilitate operation of the person support apparatus 100. For example, a healthcare professional may utilize the user input 210 to send a signal to the electronic controller 200 to command the at least one actuator 121 to raise or lower the forward column 122 and/or the rearward column 124 in the vertical direction. In embodiments, the user input 210 may include various user input devices, including, but not limited to, graphical user interfaces (GUIs), keyboards, pendants, or the like.

Referring again to FIG. 2A, the forward column 122 and the rearward column 124 may be raised and lowered in the vertical direction independent of one another such that the longitudinal frame 126 may be tilted with respect to the horizontal plane (i.e., the X-Y plane as depicted). For example, the forward column 122 may be raised with respect to the rearward column 124 in the vertical direction such that the head end of the longitudinal frame 126 is positioned higher than the foot end of the longitudinal frame 126 in the vertical direction (i.e., a reverse Trendelenburg position). Conversely, the rearward column 124 may be raised with respect to the forward column 122 in the vertical direction, such that the foot end of the longitudinal frame 126 is positioned higher than the head end of the longitudinal frame 126 in the vertical direction (i.e., a Trendelenburg position). In embodiments, both the forward column 122 and the rearward column 124 of the primary support frame 120 may be raised or lowered in the vertical direction simultaneously, thereby raising both the head end and the foot end of the longitudinal frame 126.

The support deck 130 is coupled to the longitudinal frame 126 and includes one or more segments that are positioned between the forward column 122 and the rearward column 124 in the longitudinal direction to support a patient on the person support apparatus 100. In the embodiment depicted in FIG. 2A, the support deck 130 includes an upper segment 140 positioned at the head end of the person support apparatus 100 which supports the upper body and/or the head and arms of a patient. The support deck 130 further includes a leg segment 160 positioned at the foot end of the person support apparatus 100 which supports the lower body and/or the legs of a patient. The support deck 130 includes a torso segment 150 that is positioned between the upper segment 140 and the leg segment 160 in the longitudinal direction which supports a torso and/or a mid-section of a patient.

Each of the upper segment 140, the torso segment 150, and the leg segment 160 include generally planar surfaces that support a patient on the person support apparatus 100. In some embodiments, the upper segment 140, the torso segment 150, and/or the leg segment 160 may include contoured or shaped surfaces that accommodate a patient. For example, in the embodiment depicted in FIG. 2A, the upper segment 140 includes a pillow portion 144, and arm portions 142 that accommodate a patient's head and arms, respectively. The torso segment 150 and the leg segment 160 may similarly include features and/or contours that accommodate a patient's torso and lower body, respectively.

Figure 4A:
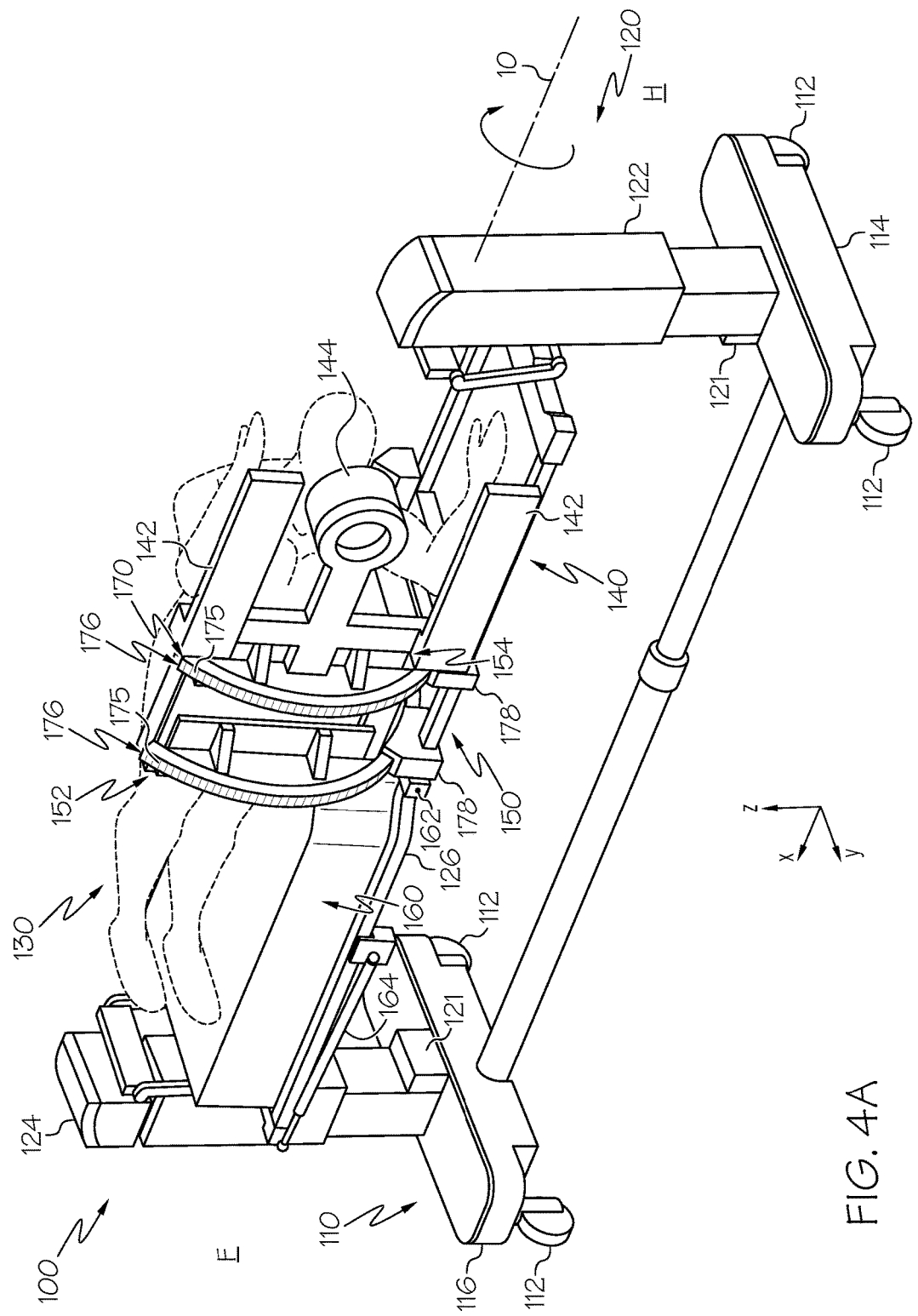
FIG. 4A schematically depicts a perspective view of the person support apparatus of FIG. 2A with a patient in a lateral position according to one or more embodiments shown or described herein.
Figure 4B:
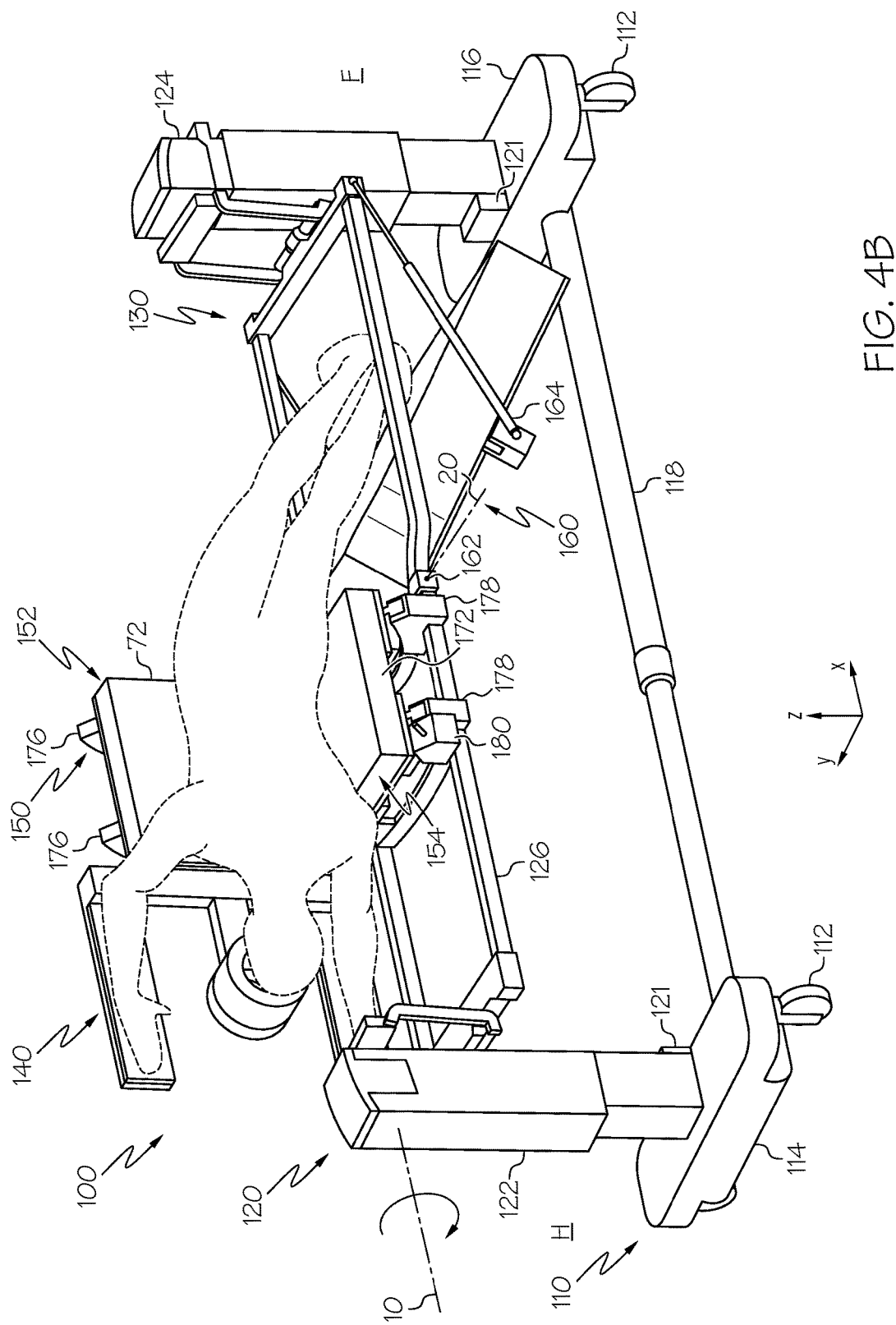
FIG. 4B schematically depicts another perspective view of the person support apparatus of FIG. 2A with a patient in a lateral position according to one or more embodiments shown or described herein.

Referring to FIG. 4B, the leg segment 160 is pivotally coupled to the longitudinal frame 126 at a leg segment pivot 162. The leg segment 160 pivots about an axis 20 at the leg segment pivot 162, where the axis 20 extends in the lateral direction. The leg segment 160 may be coupled to the longitudinal frame 126 by one or more dampers 164 that dampen movement of the leg segment 160 about the leg segment pivot 162. The one or more dampers 164 may include a variety of dampers, including, but not limited to, a linear damper or the like.

By pivoting at the leg segment pivot 162, the leg segment 160 may be lowered in the vertical direction with respect to the torso segment 150 and the upper segment 140. By lowering the leg segment 160 in the vertical direction, a patient's legs and lower body may be positioned lower than the torso of the patient, which may assist with aligning and orienting a patient during surgery. While the leg segment 160 is described and depicted as being pivotally coupled to the longitudinal frame 126, it should be understood that the leg segment 160 may be rigidly coupled to the longitudinal frame 126 and the torso segment 150 and/or the upper segment 140 may be pivotally coupled to the longitudinal frame 126.

Figure 2B:
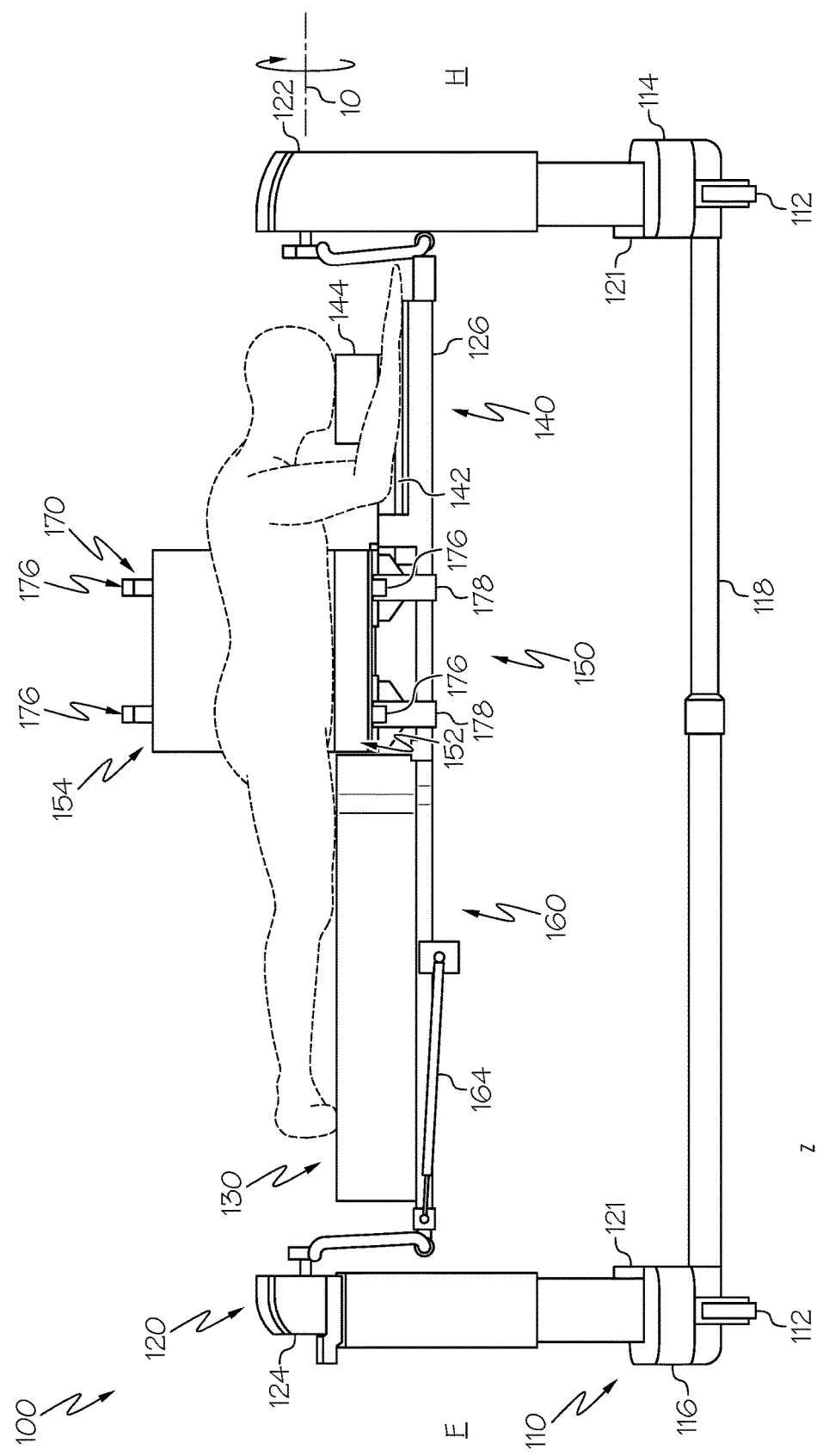
FIG. 2B schematically depicts a side view of the person support apparatus of FIG. 2A according to one or more embodiments shown or described herein.
Figure 2C:
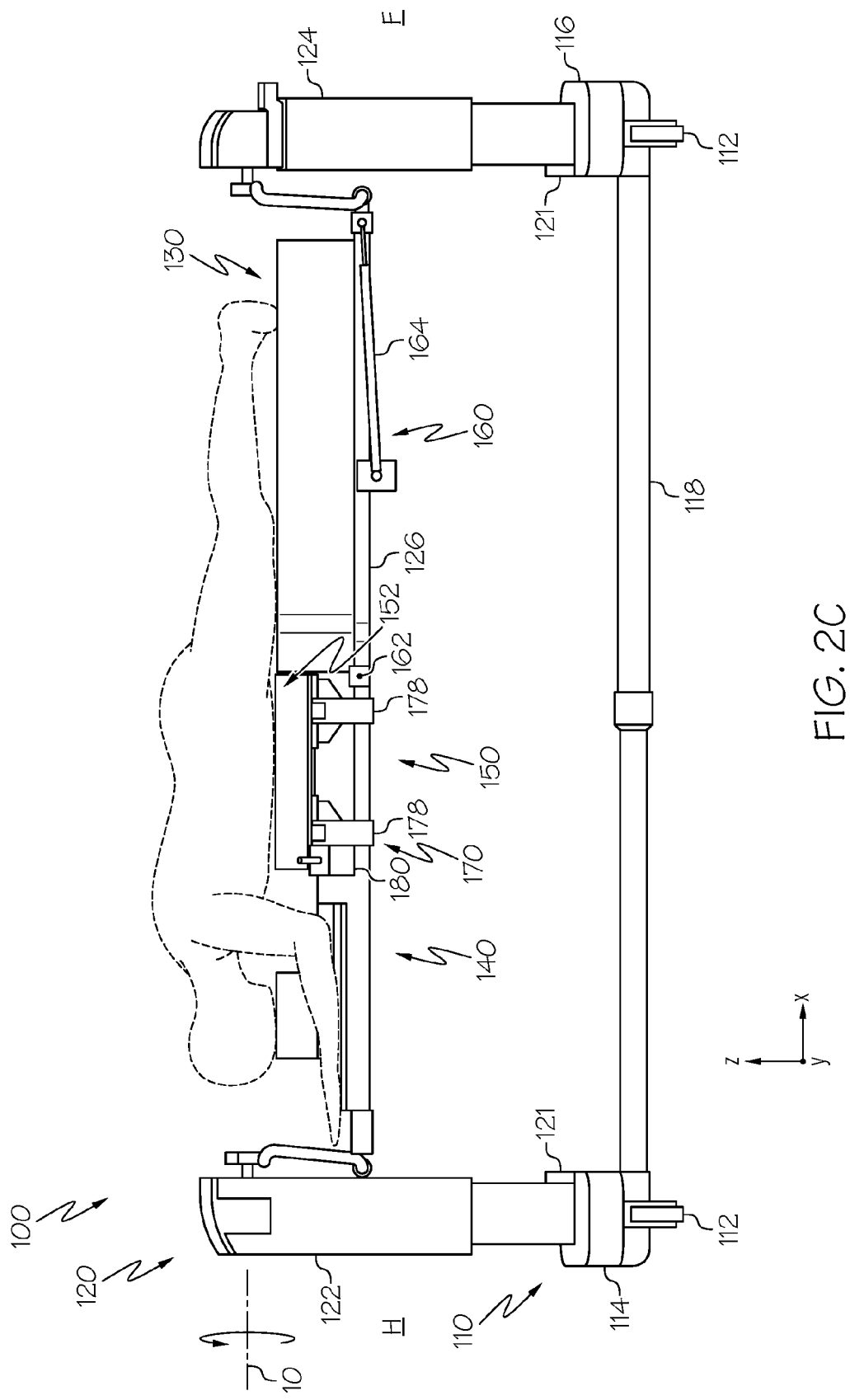
FIG. 2C schematically depicts another side view of the person support apparatus of FIG. 2A according to one or more embodiments shown or described herein.

Referring to FIG. 2B, the torso segment 150 includes one or more portions that may be selectively and severally coupled to one another. In the embodiment depicted in FIG. 1B, the torso segment 150 includes a first portion 152 that is severally coupled to a second portion 154. As shown in FIG. 2C, the second portion 154 (FIG. 2B) is severally coupled to and may be removed from the first portion 152. The first portion 152 and the second portion 154 of the torso segment 150 are oriented transverse to one another. The first portion 152 and the second portion 154 of the torso segment 150 facilitate repositioning of a patient on the person support apparatus 100, as will be described in greater detail herein.

Referring again to FIG. 2A, a repositioning assembly 170 is coupled to the torso segment 150. Additionally or alternatively, the repositioning assembly 170 may be coupled to the upper segment 140. The repositioning assembly 170 facilitates repositioning of a patient on the person support apparatus 100 and includes a pair of rocker members 176 coupled to the second portion 154 of the torso segment 150 and a pair of rocker members 176 coupled to the first portion 152 (FIG. 1B) of the torso segment 150. While the embodiment shown in FIGS. 2A and 1B depicts a pair of rocker members 176 coupled to each of the first portion 152 and the second portion 154 of the torso segment 150, it should be understood that a single rocker member 176 or multiple rocker members 176 may be coupled to each of the first portion 152 and the second portion 154 of the torso segment 150.

Ones of the rocker members 176 coupled to the first portion 152 of the torso segment 150 and ones of the rocker members 176 coupled to the second portion 154 are aligned with one another in the longitudinal direction and generally extend in a direction that is transverse to the longitudinal direction. The rocker members 176 are movably coupled to the primary support frame 120. In particular, the rocker members 176 are movably coupled to at least one guide 178 that is coupled to the longitudinal frame 126 of the primary support frame 120.

In embodiments, the rocker members 176 and/or the at least one guide 178 have a curved or arced shape such that the rocker members 176 rotate about an axis 10 with respect to the primary support frame 120, where the axis 10 extends in the longitudinal direction. The rocker members 176 and/or the at least one guide 178 include a radius of curvature that generally corresponds to a radius 12 extending from the axis 10 to the rocker members 176.

The rocker members 176 may include a toothed member 175 that is engaged with the at least one guide 178. The toothed member 175 may be positioned on an outer circumference of the rocker members 176. Alternatively or additionally, the toothed member 175 may be positioned on a side face of the rocker members 176. An actuator 180 is coupled to at least one of the guides 178 and moves the rocker members 176 with respect to the primary support frame 120. The actuator 180 may include one or more gears or screws (not depicted) that are engaged with the toothed member 175 of the rocker members 176, such that the actuator 180 and the rocker members 176 are engaged with one another in a fashion similar to a rack and pinion configuration. As the actuator 180 drives the one or more gears or screws meshed with the toothed member 175, the actuator 180 moves rocker members 176 with respect to the at least one guide 178. In embodiments, the actuator 180 may include various actuators, including, but not limited to an electric motor, a hydraulic actuator, a pneumatic actuator, or the like.

Referring to FIG. 5, the actuator 180 is communicatively coupled to the electronic controller 200. The electronic controller 200 sends signals to the actuator 180 which command the actuator 180 to move the rocker members 176 with respect to the primary support frame 120. In embodiments, the actuator 180 may include various actuators including, but not limited to an electrical motor or the like. A healthcare professional may utilize the user input 210 to send a signal to the electronic controller 200 to command the actuator 180 to move the rocker members 176 with respect to the primary support frame 120.

Referring again to FIG. 2A, the actuator 180 moves the rocker members 176 with respect to the at least one guide 178, the actuator 180 rotates the rocker members 176 about the axis 10 with respect to the primary support frame 120. As the first portion 152 and the second portion 154 of the torso segment 150 are coupled to the rocker members 176, when the rocker members 176 rotate about the axis 10 with respect to the primary support frame 120, the first portion 152 and the second portion 154 of the torso segment 150 rotate about the axis 10 with respect to the primary support frame 120.

While the actuator 180 is depicted as being positioned proximate to the torso segment 150 and as being directly engaged with the rocker members 176, it should be understood that the actuator 180 may be positioned at any suitable position on the person support apparatus 100 and may be engaged with the rocker members 176 through a variety of mechanical linkages.

The rocker members 176, the guides 178, the actuator 180, and the first portion 152 and the second portion 154 of the torso segment 150 are formed from materials such that the person support apparatus 100 may be suitable for use with a variety of medical equipment, such as an X-ray machine. In embodiments, each of the rocker members 176, the guides 178, the actuator 180, and the first portion 152 and the second portion 154 of the torso segment 150 may be formed from a variety of materials, including, but not limited to, polymers, composites, resins, carbon fiber or the like.

The person support apparatus 100, and in particular the repositioning assembly 170 of the person support apparatus 100, repositions a patient by rotating the first portion 152 and the second portion 154 of the torso segment 150 about axis 10 with respect to the primary support frame 120. For example, a patient may initially be positioned in a prone position, as depicted in FIG. 2A. During a surgical procedure, such as a spinal procedure, it may be necessary to reposition the patient from the prone position to a lateral position in which the patient is laying on his or her side, as depicted in FIG. 4A. To facilitate repositioning of the patient, the person support apparatus 100, and in particular the repositioning assembly 170, is repositionable between a first position and a second position and intermediate positions therebetween.

Referring to FIG. 2A, the person support apparatus 100 is initially positioned in a first position, in which the patient may be initially in the prone position. In the first position, the first portion 152 of the torso segment 150 is substantially co-planar with the horizontal plane (i.e., the X-Y plane as depicted) and may be co-planar with the longitudinal frame 126 of primary support frame 120. The first portion 152 of the torso segment 150 may also be substantially co-planar with the upper segment 140 and/or the leg segment 160 when the person support apparatus 100 is in the first position. The second portion 154 of the torso segment 150 is severally coupled to and is oriented transverse to the first portion 152 of the torso segment 150. Accordingly, the second portion 154 of the torso segment 150 is also oriented transverse to the longitudinal frame 126 in the first position.

Figure 3:
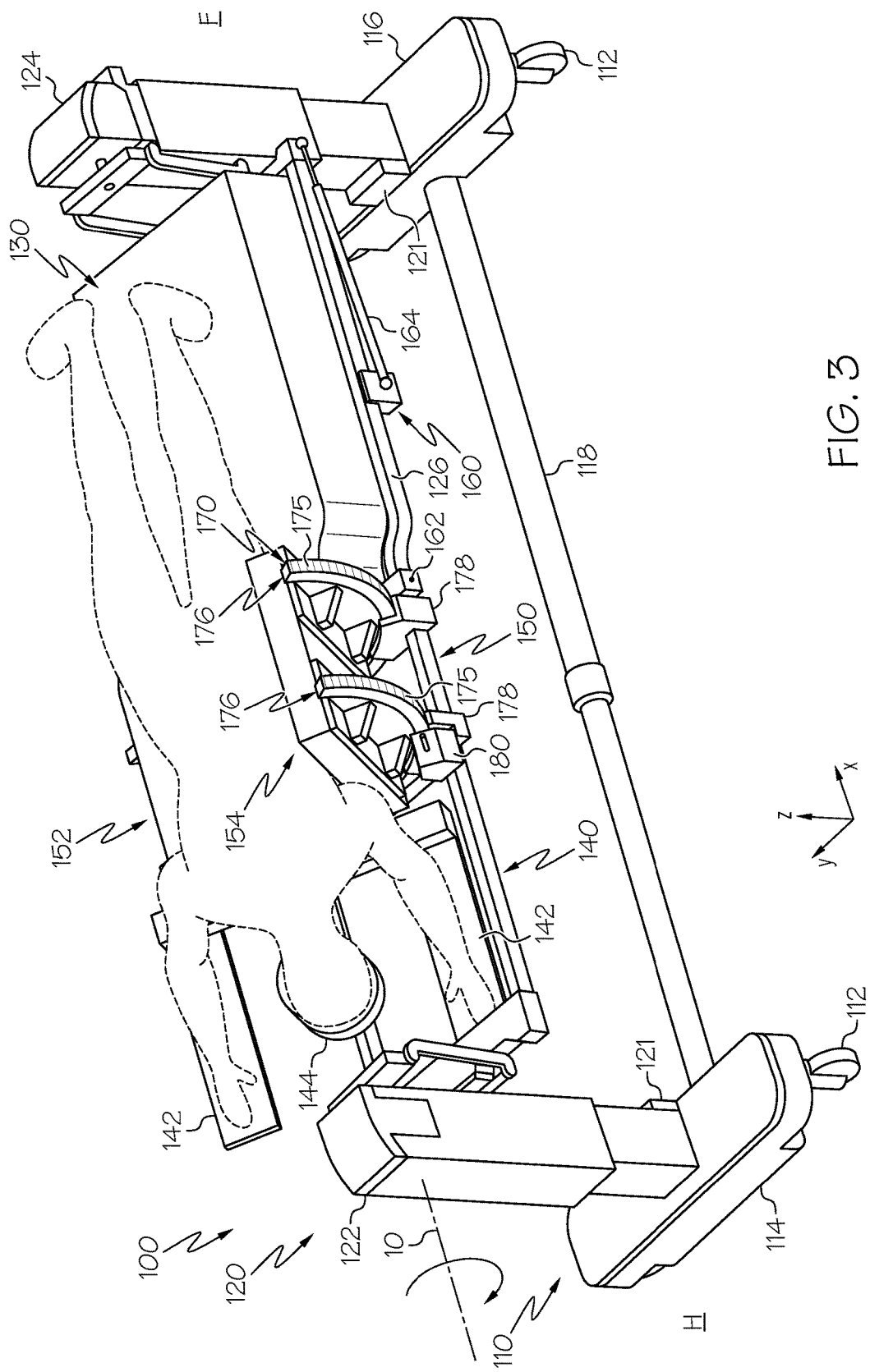
FIG. 3 schematically depicts a perspective view of the person support apparatus of FIG. 2A repositioning a patient from a prone position to a lateral position according to one or more embodiments shown or described herein.

Referring to FIG. 3, to reposition the person support apparatus 100 between the first position and the second position, the actuator 180 moves one of the rocker members 176 and the first portion 152 and/or the second portion 154 of the torso segment 150 that are coupled to the rocker members 176. In particular, the actuator 180 rotates the rocker members 176 and the first portion 152 and the second portion 154 about the axis 10. In the embodiment depicted in FIG. 3, the upper segment 140 is coupled to the first portion 152 of the torso segment 150 such that the upper segment 140 rotates about the axis 10 with the first portion 152 of the torso segment 150. In other embodiments, the torso segment 150 is not coupled to either the upper segment 140 or the leg segment 160 such that the torso segment 150 rotates about the axis 10 while the upper segment 140 and the leg segment 160 remain stationary.

The rocker member 176 that is coupled to the first portion 152 continues to rotate and the actuator 180 engages the rocker member 176 that is coupled to the second portion 154 of the torso segment 150. Once engaged with the rocker member 176 that is coupled to the second portion 154 of the torso segment 150, the actuator 180 continues to rotate the torso segment 150 to reposition the person support apparatus 100 into the second position.

Referring to FIG. 4A, the person support apparatus 100 is depicted in the second position. In the second position, the second portion 156 of the torso segment 150 is substantially co-planar with the horizontal plane (i.e., the X-Y plane as depicted), thereby positioning the patient in a lateral position. In particular, the patient's side is positioned on the second portion 156 of the torso segment 150, which is substantially co-planar with the longitudinal frame 126 such that the patient is laying on his or her side. As described above, the second portion 154 of the torso segment 150 is oriented transverse to the first portion 152 of the torso segment 150. Accordingly, when the person support apparatus 100 is in the second position, the first portion 152 is oriented transverse to the longitudinal frame 126. Once the person support apparatus 100 is in the second position, the first portion 152 of the torso segment 150 may be removed from the second portion 154.

While the person support apparatus 100 is described and depicted as showing the repositioning assembly 170 moving a patient between a prone position and a lateral position, it should be understood that the person support apparatus 100 may be utilized to move a patient between additional rotational positions. For example, the person support apparatus 100 may be utilized to reposition a patient between the lateral position, as shown in FIG. 4A and a supine position (not depicted), or between the supine position and a lateral position. Further, while the actuator 180 is depicted as rotating the torso segment 150 in the clockwise direction about the axis 10, it should be understood that the actuator 180 may rotate the torso segment 150 in the counterclockwise direction about the axis 10.

FIG. 6A schematically depicts an example system 300 including an imaging device 302 and a person support apparatus 304. As discussed above with respect to FIGS. 1A and 1B, at least one of the imaging device 302 and the persons support apparatus includes a sensor 306 for detecting one or more optical markers disposed on the person support apparatus 304, the imaging device 302 and/or a patient.

In the particular embodiment shown in FIG. 6A, for example, the person support apparatus 304 includes one or more optical sensors attached to one or more locations of the support apparatus 304. In this example, an optical sensor 306 is disposed at an end 308 of the person support apparatus 304 and is aimed toward a central portion 310 of the person support apparatus 304 where a patient would be placed on the apparatus, such as during a surgical procedure.

The optical sensor(s) 306, in one embodiment for example, may comprise an infrared laser projector combined with a complementary metal oxide semiconductor (CMOS) sensor, such as is used in a Kinect™ optical sensor sold by Microsoft Corporation of Redmond, Wash. In this embodiment, the optical sensor captures video data in three dimensions (3D) under ambient light conditions and is adapted to determine depth of an optical marker or other feature of the imaging device 302. The optical sensor(s) may include using one or more cameras and/or other sensors for detecting one or more objects or markers and/or accessing a data representation of the area including the person support apparatus (e.g., an internally stored map or look up table) or other representation of the surrounding operational area (e.g., surgical room). Although various embodiments are shown using optical markers disposed on the imaging device, person support apparatus and/or patient, the optical sensor may also use an object recognition process or algorithm, such as a scale-invariant feature transform (SIFT) algorithm, or other object recognition processes. A SIFT algorithm, for example, uses computer vision technology to detect and describe local features in images. Points on an object may be extracted to provide a feature description of the object. This description, extracted from a training image, may then be used to identify a location corresponding to the imaging device 302 relative to the person support apparatus and/or patient. Features extracted from a training image in various implementations may be detectable even under changes in image scale, noise and illumination. Other implementations of optical sensors include motion capture systems (e.g., for 3D animation, biomechanics, virtual reality, computer vision, engineering) such as OptiTrack motion capture camera-based systems sold by NaturalPoint, Inc. of Corvallis, Oreg.

The imaging device 302, in this embodiment, includes one or more optical markers 312 disposed on the device 302. In the embodiment shown in FIG. 6A, for example, the optical markers 312 are disposed on a portion of the C-arm of the imaging device. The optical markers 312, however, may be disposed in other location(s) on the imaging device 302. The optical markers 312, for example, may include light reflectors (passive markers such as retroreflectors) or light emitters (active markers such as light emitting diodes (LEDs)). In addition, the optical markers may include single markers disposed at one or more locations of the imaging device, person support apparatus and/or patient or may include a plurality of markers disposed in a pattern on one or more locations of the imaging device, person support apparatus and/or patient.

Although FIG. 6A shows the optical sensor 306 disposed on an end of the person support apparatus 304, one or more optical sensor(s) 306 may be disposed at any location of the person support apparatus 304 that is fixed in location with respect to a patient on the person support apparatus 304.

FIG. 6B schematically depicts an example system 320 including an imaging device 322 and a person support apparatus 324. As discussed above with respect to FIGS. 1A and 1B, at least one of the imaging device 322 and the persons support apparatus 324 includes a sensor 326 for detecting one or more optical markers 332 disposed on the person support apparatus 324, the imaging device 322 and/or a patient.

In the particular embodiment shown in FIG. 6B, for example, the imaging device 322 includes one or more optical sensors 326 attached to one or more locations of the imaging device 322. In this example, an optical sensor 326 is disposed along a C-arm of the imaging device 322 and is aimed toward one or more markers 332 disposed on the person support apparatus 304 and/or a patient located on the apparatus, such as during a surgical procedure.

The optical sensor(s) 326, in one embodiment for example, may comprise an infrared laser projector combined with a CMOS sensor, such as is used in a Kinect™ optical sensor sold by Microsoft Corporation of Redmond, Wash. In this embodiment, the optical sensor captures video data in three dimensions (3D) under ambient light conditions and is adapted to determine depth of an optical marker or other feature of the imaging device 332. The optical sensor(s) may include one or more cameras and/or other sensors for detecting one or more objects or markers and/or accessing a data representation of the area including the person support apparatus (e.g., an internally stored map or look up table) or other representation of the surrounding operational area (e.g., surgical room). Although various embodiments are shown using optical markers disposed on the imaging device, person support apparatus and/or patient, the optical sensor may also use an object recognition process or algorithm, such as a scale-invariant feature transform (SIFT) algorithm, or other object recognition processes. A SIFT algorithm, for example, uses computer vision technology to detect and describe local features in images. Points on an object may be extracted to provide a feature description of the object. This description, extracted from a training image, may then be used to identify a location corresponding to the person support apparatus 324 and/or patient relative to the imaging device 322. Features extracted from a training image in various implementations may be detectable even under changes in image scale, noise and illumination.

The person support apparatus 324, in this embodiment, includes one or more optical markers 332 disposed on the apparatus 324. The optical markers 332, for example, may include light reflectors (passive markers such as retroreflectors) or light emitters (active markers such as light emitting diodes (LEDs)). In addition, the optical markers may include single markers disposed at one or more locations of the imaging device, person support apparatus and/or patient or may include a plurality of markers disposed in a pattern on one or more locations of the imaging device, person support apparatus and/or patient.

Although FIG. 6B shows the optical sensor 326 disposed on a C-arm of the imaging device 322, one or more optical sensor(s) 326 may be disposed at any location of the imaging device 322.

Figure 7A:
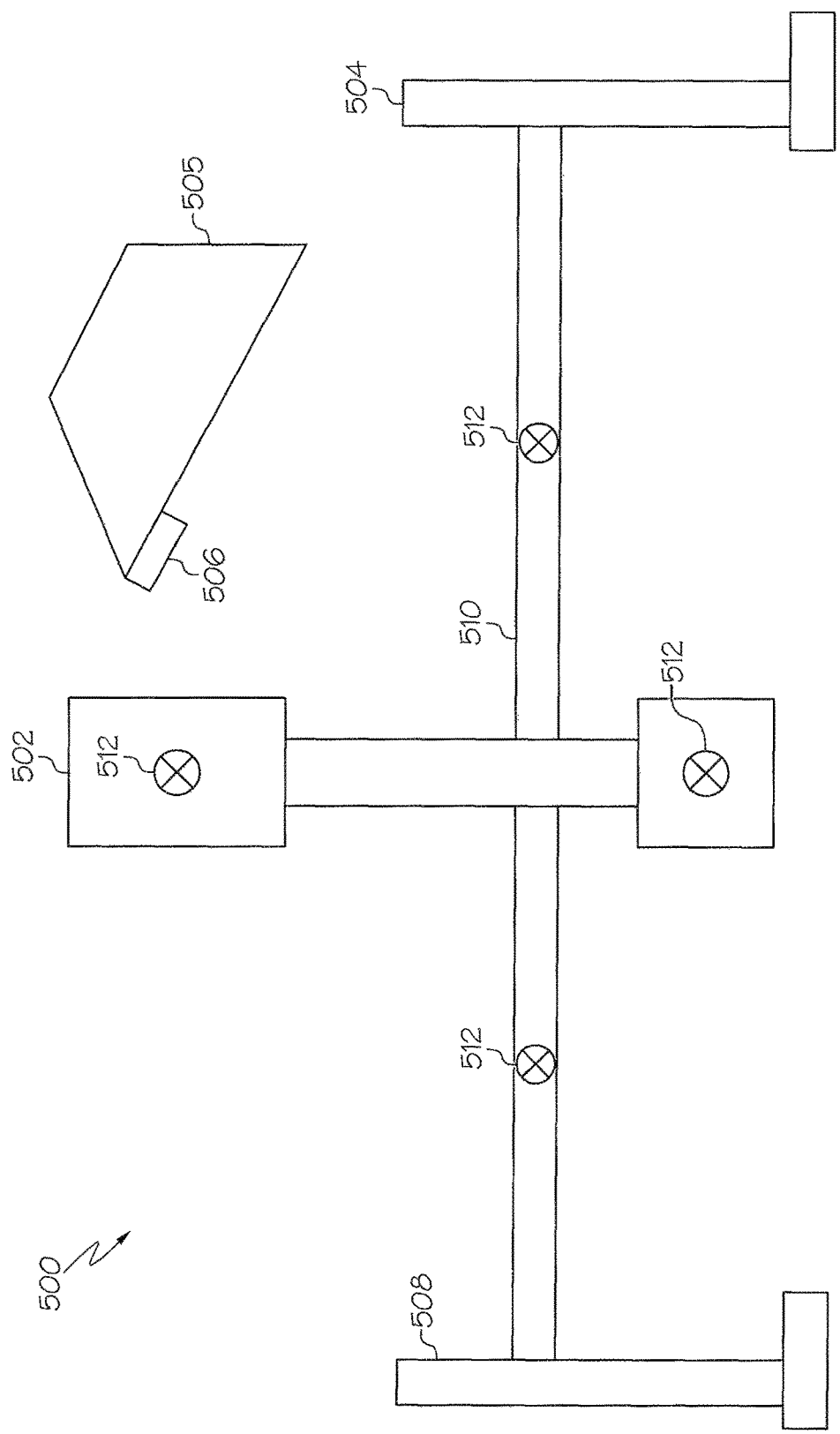
FIG. 7A schematically depicts an example system including a medical imaging device, a person support apparatus and a surgical light according to one or more embodiments shown or described herein.

FIG. 7A schematically depicts another example system 500 including an imaging device 502, a person support apparatus 504 and a surgical light 505 (or other component or device within a surgical, diagnostic or treatment room). As discussed above with respect to FIGS. 1A and 1B, at least one of the imaging device 502, the person support apparatus 504 and the surgical light 505 includes a sensor 506 for detecting one or more optical markers 512 disposed on the person support apparatus 504, the imaging device 502, the surgical light 505 and/or a patient.

Although FIG. 7A shows the sensor 506 disposed on the surgical light 505 in this particular embodiment, the sensor 506 may be disposed on any other device, component, structure or feature adjacent to or nearby a surgical, diagnostic or treatment area. For example, the sensor 506 may be connected to or disposed nearby any device, component, structure and/or feature in a surgical room, such as but not limited to the surgical light, an anesthesia machine, a monitor, a table, a shelf, a wall, a ceiling, a floor, a post, a beam or other device, component, structure and/or feature.

In the particular embodiment shown in FIG. 7A, for example, the surgical light 505 includes one or more optical sensors attached to one or more locations of the surgical light 505. In this example, an optical sensor 506 is disposed generally along a surface of the surgical light facing the person support apparatus 504 and is aimed toward a central portion 510 of the person support apparatus 504 where a patient would be placed on the apparatus, such as during a surgical procedure. The optical sensor 506 is also aimed generally towards one or more optical markers 512 disposed on the imaging device 502.

The optical sensor(s) 506, in one embodiment for example, may comprise an infrared laser projector combined with a complementary metal oxide semiconductor (CMOS) sensor, such as is used in a Kinect™ optical sensor sold by Microsoft Corporation of Redmond, Wash. In this embodiment, the optical sensor captures video data in three dimensions (3D) under ambient light conditions and is adapted to determine depth of an optical marker or other feature of the imaging device 502, the person support apparatus 504 and/or patient. The optical sensor(s) may include using one or more cameras and/or other sensors for detecting one or more objects or markers and/or accessing a data representation of the area including the imaging device, the person support apparatus and/or the patient (e.g., an internally stored map or look up table) or other representation of the surrounding operational area (e.g., surgical room). Although various embodiments are shown using optical markers disposed on the imaging device, person support apparatus and/or patient, the optical sensor may also use an object recognition process or algorithm, such as a scale-invariant feature transform (SIFT) algorithm, or other object recognition processes. A SIFT algorithm, for example, uses computer vision technology to detect and describe local features in images. Points on an object may be extracted to provide a feature description of the object. This description, extracted from a training image, may then be used to identify a location corresponding to the imaging device 502, the person support apparatus and/or patient relative to the surgical light 505. Features extracted from a training image in various implementations may be detectable even under changes in image scale, noise and illumination. Other implementations of optical sensors include motion capture systems (e.g., for 3D animation, biomechanics, virtual reality, computer vision, engineering) such as OptiTrack motion capture camera-based systems sold by NaturalPoint, Inc. of Corvallis, Oreg.

The imaging device 502 and the person support apparatus 504, in this embodiment, include one or more optical markers 512 disposed on the device 502 and person support apparatus 504. In the particular embodiment shown in FIG. 7A, for example, the optical markers 512 are disposed on a portion of a C-arm of the imaging device 502 and on a central portion 510 of the person support apparatus 504. The optical markers 512, however, may be disposed in other location(s) on the imaging device 502 and/or the person support apparatus 504. The optical markers 512, for example, may include light reflectors (passive markers such as retroreflectors) or light emitters (active markers such as light emitting diodes (LEDs)). In addition, the optical markers may include single markers disposed at one or more locations of the imaging device, person support apparatus and/or patient or may include a plurality of markers disposed in a pattern on one or more locations of the imaging device, person support apparatus and/or patient.

Although FIG. 7A shows the optical sensor 506 disposed along a surface of the surgical light 505, one or more optical sensor(s) 506 may be disposed at any location of the surgical light 505 or on any other device, component, structure or feature adjacent to or nearby a surgical, diagnostic or treatment area. In one embodiment, for example, the surgical light 505 and/or other device, component, structure or feature adjacent to or nearby a surgical, diagnostic or treatment area is fixed in location with respect to a patient on the person support apparatus 504.

FIG. 7B schematically depicts an example system 520 including an imaging device 522, a person support apparatus 524 and a surgical light 525. As discussed above with respect to FIGS. 1A and 1B, at least one of the imaging device 522, the person support apparatus 524 and the surgical light 525 includes a sensor 526 for detecting one or more optical markers 532 disposed on the person support apparatus 524, the imaging device 522, the surgical light 525 and/or a patient.

Although FIG. 7B shows the sensor 526 disposed on the imaging device 522 in this particular embodiment, the sensor 526 may be disposed on any other device, component, structure or feature adjacent to or nearby a surgical, diagnostic or treatment area. For example, the sensor 526 may be connected to or disposed nearby any device, component, structure and/or feature in a surgical room, such as but not limited to the surgical light, an anesthesia machine, a monitor, a table, a shelf, a wall, a ceiling, a floor, a post, a beam or other device, component, structure and/or feature.

Similarly, although the optical marker(s) 532 are shown disposed on the person support apparatus 524 and surgical light 525, one or more optical markers 532 may be disposed on or coupled to any other device, component, structure or feature adjacent to or nearby a surgical, diagnostic or treatment area. For example, the optical marker(s) 532 may be connected to or disposed nearby any device, component, structure and/or feature in a surgical room, such as but not limited to the surgical light, an anesthesia machine, a monitor, a table, a shelf, a wall, a ceiling, a floor, a post, a beam or other device, component, structure and/or feature.

In the particular embodiment shown in FIG. 7B, for example, the imaging device 522 includes one or more optical sensors 526 attached to one or more locations of the imaging device 522. In this example, an optical sensor 526 is disposed along a C-arm of the imaging device 522 and is aimed toward one or more markers 532 disposed on the person support apparatus 504, the surgical light 525 and/or a patient located on the apparatus, such as during a surgical procedure.

The optical sensor(s) 526, in one embodiment for example, may comprise an infrared laser projector combined with a CMOS sensor, such as is used in a Kinect™ optical sensor sold by Microsoft Corporation of Redmond, Wash. In this embodiment, the optical sensor 526 captures video data in three dimensions (3D) under ambient light conditions and is adapted to determine depth of an optical marker 532 or other feature of the person support apparatus 524 or surgical light 525. The optical sensor(s) may include one or more cameras and/or other sensors for detecting one or more objects or markers and/or accessing a data representation of the area including the person support apparatus or surgical light (e.g., an internally stored map or look up table) or other representation of the surrounding operational area (e.g., surgical room). Although various embodiments are shown using optical markers disposed on the imaging device, person support apparatus, surgical light and/or patient, the optical sensor may also use an object recognition process or algorithm, such as a scale-invariant feature transform (SIFT) algorithm, or other object recognition processes. A SIFT algorithm, for example, uses computer vision technology to detect and describe local features in images. Points on an object may be extracted to provide a feature description of the object. This description, extracted from a training image, may then be used to identify a location corresponding to the person support apparatus 524 and/or patient relative to the imaging device 522. Features extracted from a training image in various implementations may be detectable even under changes in image scale, noise and illumination.

The person support apparatus 524 and surgical light 525, in this embodiment, include one or more optical markers 532 disposed on the apparatus 524 and/or light 525. The optical markers 532, for example, may include light reflectors (passive markers such as retroreflectors) or light emitters (active markers such as light emitting diodes (LEDs)). In addition, the optical markers may include single markers disposed at one or more locations of the imaging device, person support apparatus, surgical light and/or patient or may include a plurality of markers disposed in a pattern on one or more locations of the imaging device, person support apparatus, surgical light and/or patient.

Although FIG. 7B shows the optical sensor 526 disposed on a C-arm of the imaging device 522, one or more optical sensor(s) 526 may be disposed at any location of the imaging device 522.

Figure 8:
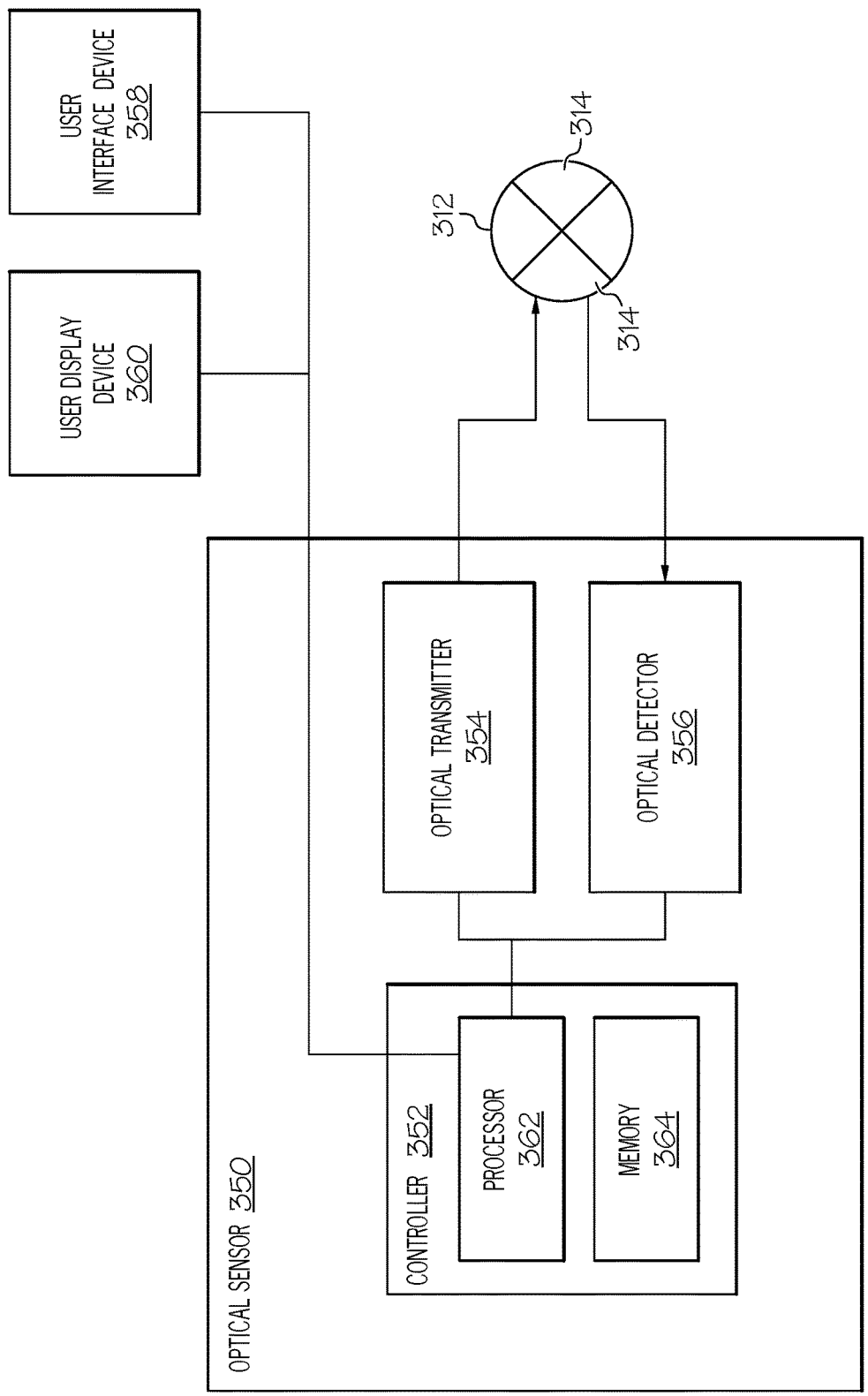
FIG. 8 schematically depicts an example optical sensor of a system for locating a medical imaging device according to one or more embodiments shown or described herein.

Referring to FIG. 8, an example optical sensor 350 includes a controller 352 communicatively coupled to an optical transmitter 354, an optical detector 356, a user interface device 358 and a user display device 360. The controller 352, for example, includes a processor 362 and a memory 364 storing computer readable and executable instructions, which, when executed by the processor, facilitate operation of the optical sensor 350. In particular, the controller 352 sends a signal to the optical transmitter 354 to transmit a signal, such as an infrared laser signal toward one or more optical markers 332 disposed on at least one of an imaging device, person support apparatus and/or a patient disposed on the person support apparatus. The controller 352, for example, may activate the optical transmitter 354 in response to an input received from a user (e.g., a surgeon) via the user interface device 358 requesting the image sensor to detect a location of an imaging device, a person support apparatus and/or a patient disposed on the person support apparatus.

Where the optical marker(s) 312 include a reflective surface 314 (e.g., a retroreflective surface), the optical detector 356 receives the signal reflected from the reflective surface 314 of the optical marker 312. The controller 352 receives a signal from the optical detector 356 and determines a location of the optical marker(s) 312 relative to the optical sensor 350. The controller 352 may also display a representation of the relative location on the user display device 360.

In one embodiment, for example, the optical transmitter 354 may include an infrared or other wavelength laser transmitter that emits an eye-safe wavelength laser signal toward one or more optical markers. The optical detector 356, for example, may comprise a charge-coupled device (CCD) sensor, a CMOS sensor or other optical detector adapted to detect a reflected or dispersed optical signal generated by the optical transmitter 354 and reflected by the optical marker(s) 312. The optical detector 356 is further adapted to provide one or more signals to the controller 352 representative of the received reflected signal.

The user interface device 358 includes a device that allows a user to input various parameters into the electronic controller 352 to facilitate operation of the system to locate an imaging device relative to a person support apparatus and/or patient. For example, a healthcare professional may utilize the user interface device 358 to send a signal to the electronic controller 352 to command the optical sensor 350 to determine a location of an imaging device relative to the person support apparatus and/or the patient. In embodiments, the user interface device 358 may include various user input devices, including, but not limited to, graphical user interfaces (GUIs), keyboards, pendants, or the like. The controller 352 may further display a result or representation of the determined location of the imaging device relative to the persons support apparatus and/or patient on the user display device 360. The user display device 360, for example, may include a monitor, printer, display or other display device through which the controller may identify the relative location to a user. In one embodiment, for example, the controller 352 may provide an offset location for the imaging device relative to the person support apparatus and/or patient compared to a prior relative location determination. Where a health care professional took an initial image or reading (e.g., an X-ray, CT scan, MRI image or the like) using the imaging device, the controller can provide a determined offset from that initial location where the healthcare professional is attempting to align the imaging device and the person support apparatus and/or patient for a subsequent image of the same location/orientation of the patient. In another embodiment, the controller 352 may cause the user display device to provide a video image (actual or computer-generated) of the current location of the imaging device relative to a still image (actual or computer-generated) of the imaging device, person support apparatus and/or patient during a prior imaging session. In this manner, the healthcare professional can align the current video image with the prior still image to get an accurate, repeat image of the patient.

Figure 9:
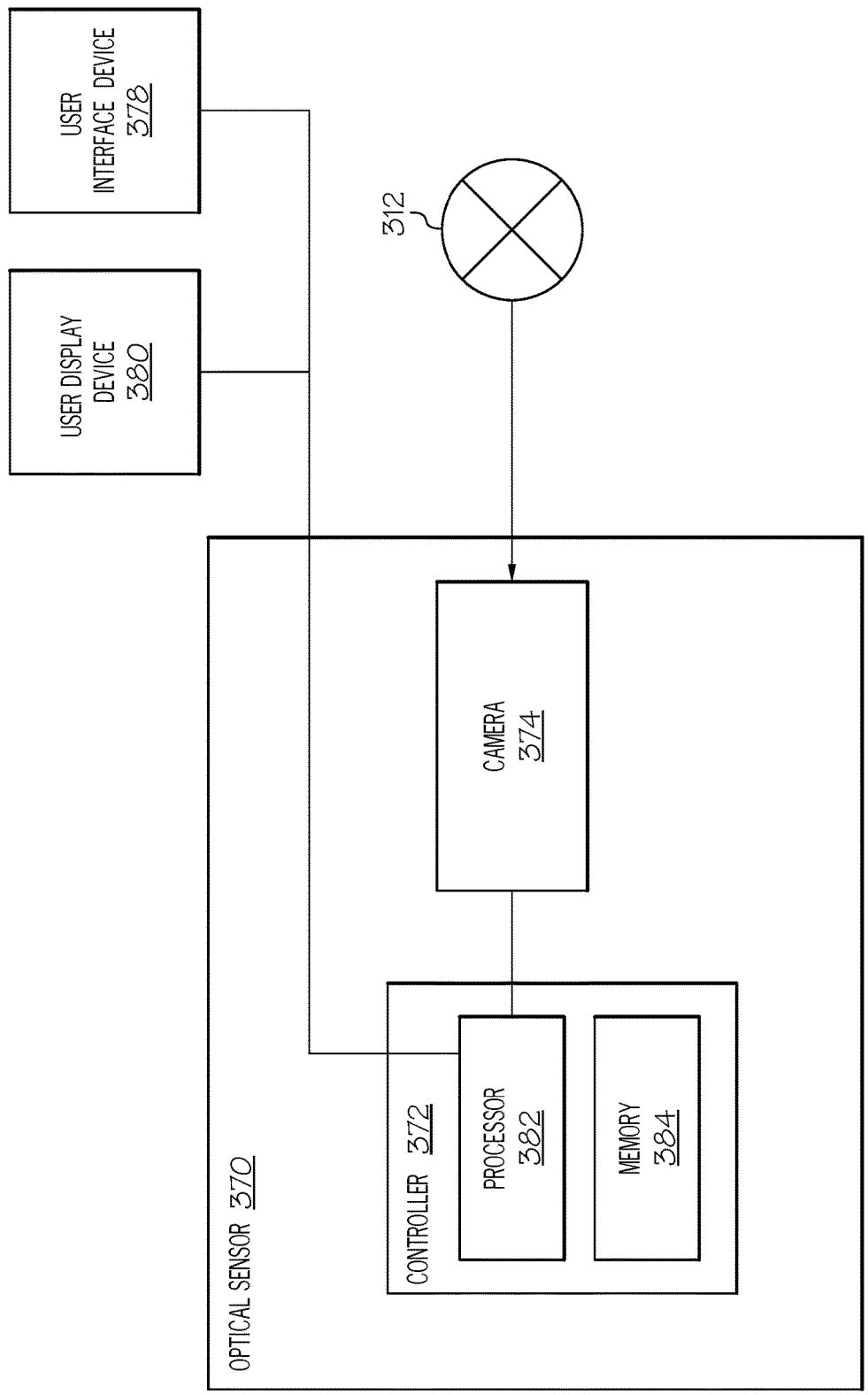
FIG. 9 schematically depicts another example optical sensor of a system for locating a medical imaging device according to one or more embodiments shown or described herein.

Referring to FIG. 9, another example of an optical sensor 370 includes a controller 352 communicatively coupled to a camera 374, a user interface device 378 and a user display device 380. The controller 372, for example, includes a processor 382 and a memory 384 storing computer readable and executable instructions, which, when executed by the processor, facilitate operation of the optical sensor 370. In particular, the controller 372 sends a signal to the camera 374 to capture a video and/or still image signal including one or more optical markers 332 disposed on at least one of an imaging device, person support apparatus and/or a patient disposed on the person support apparatus. The controller 372, for example, may activate the camera 374 in response to an input received from a user (e.g., a surgeon) via the user interface device 378 requesting the image sensor to detect a location of an imaging device, a person support apparatus and/or a patient disposed on the person support apparatus.

A detector 376 of the camera 374 receives the captured image (video or still) including the optical marker(s) 312. The controller 372 receives a signal from the camera 374 and determines a location of the optical marker(s) 312 relative to the optical sensor 350 (e.g., using an object recognition process such as described above). The controller 372 may also display a representation of the relative location on the user display device 380.

In one embodiment, for example, the camera 374 may include a CCD, CMOS or other image detector adapted to capture an image (video or still). The camera 374 is further adapted to provide one or more signals to the controller 372 representative of the received reflected signal.

The user interface device 378 includes a device that allows a user to input various parameters into the electronic controller 372 to facilitate operation of the system to locate an imaging device relative to a person support apparatus and/or patient. For example, a healthcare professional may utilize the user interface device 378 to send a signal to the electronic controller 372 to command the optical sensor 370 to determine a location of an imaging device relative to the person support apparatus and/or the patient. In embodiments, the user interface device 378 may include various user input devices, including, but not limited to, graphical user interfaces (GUIs), keyboards, pendants, or the like. The controller 372 may further display a result or representation of the determined location of the imaging device relative to the persons support apparatus and/or patient on the user display device 380. The user display device 380, for example, may include a monitor, printer, display or other display device through which the controller may identify the relative location to a user. In one embodiment, for example, the controller 372 may provide an offset location for the imaging device relative to the person support apparatus and/or patient compared to a prior relative location determination. Where a health care professional took an initial image or reading (e.g., an X-ray, CT scan, MRI image or the like) using the imaging device, the controller can provide a determined offset from that initial location where the healthcare professional is attempting to align the imaging device and the person support apparatus and/or patient for a subsequent image of the same location/orientation of the patient. In another embodiment, the controller 372 may cause the user display device to provide a video image of the current location of the imaging device relative to a still image taken of the imaging device, person support apparatus and/or patient during a prior imaging session. In this manner, the healthcare professional can align the current video image with the prior still image to get an accurate, repeat image of the patient.

Figure 10:
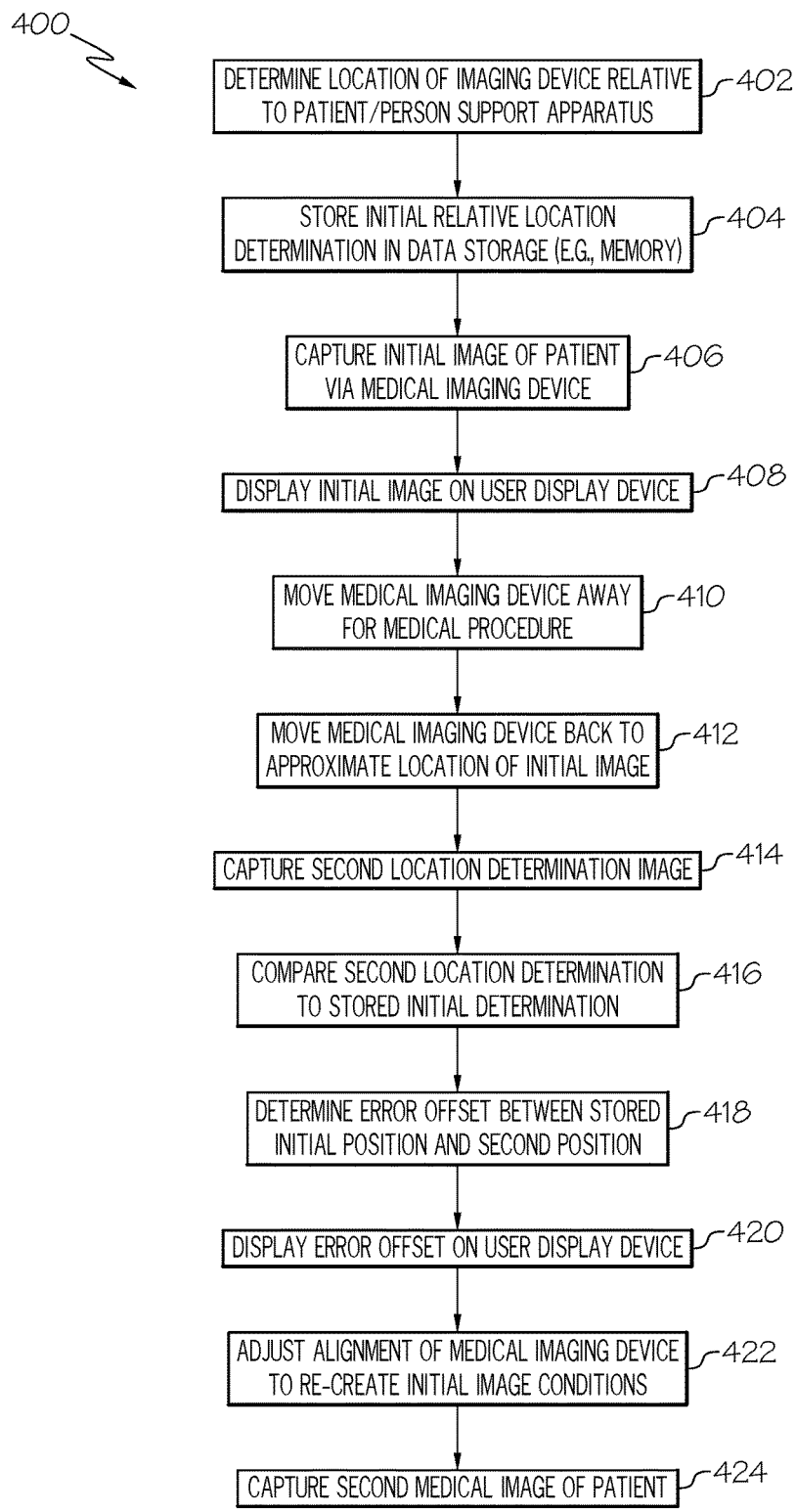
FIG. 10 schematically depicts an example process for locating a medical imaging device relative to a patient and/or person support apparatus according to one or more embodiments shown or described herein.

Referring to FIG. 10, an example process 400 for locating an imaging device relative to a patient and/or person support apparatus is provided. In this embodiment, a location of the imaging device is determined relative to a patient and/or a person support apparatus in operation 402. An optical sensor disposed on the imaging device or the person support apparatus, for example, may detect one or more optical markers disposed on the person support apparatus/patient or the imaging device, respectively and determine a location of the imaging device relative to the person support apparatus and/or patient. As described above with reference to FIGS. 8 and 9, the determination may be made based on a transmitted signal reflected off of an optical marker and/or via an image recognition process using one or more images (video or still) taken by a camera of the optical sensor.

An initial relative location determination (e.g., an image, coordinate identification or the like) may be stored, such as in memory 364, 384 or other volatile or non-volatile data storage (e.g., flash, RAM, ROM, disk drive, SRAM, DRAM or the like) of an optical sensor, for later comparison by a controller 352, 372 of the optical sensor in operation 404.

An initial image of a patient is taken in operation 406 by the imaging device at the initial relative location. This initial image may be used by a healthcare professional, such as a surgeon or surgical assistant in a number of ways. The initial image, for example, may depict a pre-surgical image (X-ray, CT scan, MRI image or the like) to show the surgeon or surgical assistant a location of interest for a surgical procedure. In this example, the image may be displayed on a user display device or printed out for reference during the surgical procedure in operation 408. In this manner, the imaging device (e.g., C-arm radiographic imaging device) may be moved out of the way during the surgical procedure and the image may be used to initiate and/or during a surgical procedure in operation 410.

When the surgical procedure is complete or during the surgical procedure, the imaging device may be moved back into an approximate location of the initial image position in operation 412. A second location determination image is taken in operation 414 and is compared to the initial location determination stored in memory or other data storage in operation 416.

The comparison operation, in one embodiment, may include determining an error offset (e.g., difference in a Cartesian coordinate value (x,y,z)) in operation 418 and may be displayed on a user display device (e.g., a monitor, display or print out) for review by a healthcare professional in operation 420. In another embodiment, an image taken with the imaging device disposed at the second location may be compared with an initial image taken at the initial position. The image, for example, may show a video image of the imaging device, person support apparatus and/or patient at the second location over-layed on top of a prior still image of the imaging device, person support apparatus and/or patient taken at the initial image location.

Figure 11:
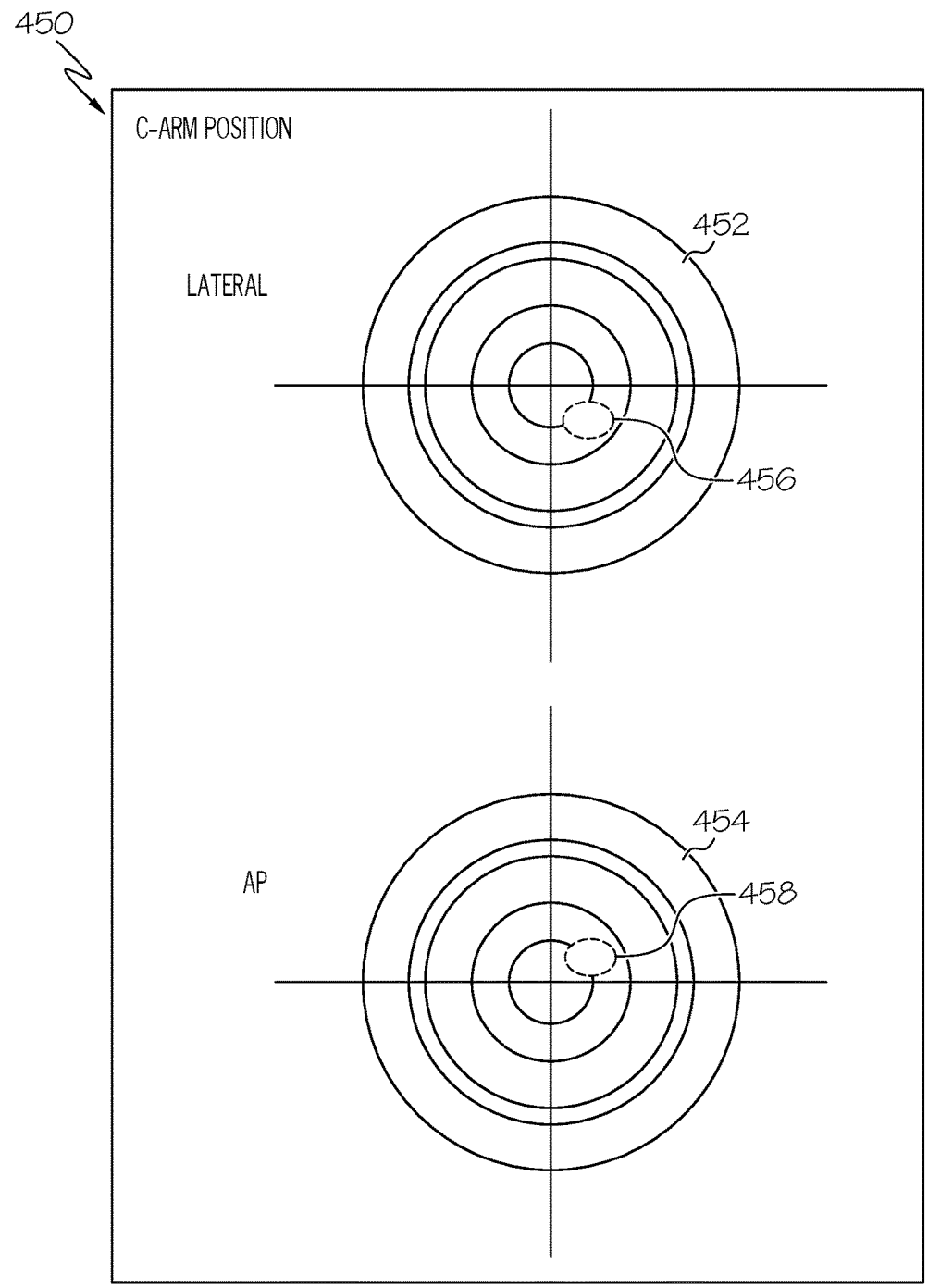
FIG. 11 schematically depicts an example user display of a system for locating a medical imaging device relative to a patient and/or person support apparatus according to one or more embodiments shown or described herein.

Referring to FIG. 11, an example graphic representation 450 of a user display showing alignment of a C-arm radiographic imaging device is shown. In this display, for example, a first target grid 452 corresponding to lateral placement of the imaging device at an initial position is displayed. A second target grid 454 corresponding to anteroposterior (AP) placement of the imaging device at the initial position is also displayed. The current location of the imaging device in a lateral placement is shown via a first lateral tracking indicator 456 that moves relative to the first target grid 452 with detected movement of the imaging device. The current location of the imaging device in an AP placement of the imaging device is also shown via a second AP tracking indicator 458 that also moves relative to the second target grid 454 with detected movement of the imaging device. Although the example display shown in FIG. 11 is a computer-generated representation of the location of the imaging device relative to the person support apparatus and patient, the display may also include actual images captured by one or more optical sensor(s) of the system.

In this manner, the healthcare professional may adjust the alignment of the imaging device, person support apparatus and/or patient (manually or automatically via a controller and one or more actuators) to re-create the initial image conditions in operation 422 prior to actually taking a second radiographic image with the imaging device. Thus, multiple, sequential images using the radiographic imaging device do not need to be taken to align the imaging device relative to the person support apparatus and/or patient and the patient and healthcare professionals present can be exposed to significantly less radiation than would otherwise occur if recursive radiographic images were used to align the radiographic imaging device.

Once the imaging device is aligned (e.g., within a predetermined error tolerance or by the healthcare professional to his or her professional judgment), a second radiographic image is taken of the patient in operation 424.

It should now be understood that system and process of locating a medical imaging device (e.g., a radiographic imaging device) relative to a person support apparatus and/or a patient include an optical sensor disposed at the person support apparatus and/or the medical imaging device. In embodiments, optical markers may also be disposed on one or more of the medical imaging device, the person support apparatus and/or patient for determining the relative location of the imaging device and the person support apparatus and/or patient. In other embodiments, an optical sensor may use image recognition processes to determine the relative locations. By locating and positioning the medical imaging device without taking recursive images (e.g., radiographic images) to position the device, the medical imaging device can be positioned for a subsequent image without exposing the patient and healthcare professionals to additional radiation generated while positioning the medical imaging device, thereby reducing risk to the patient and the medical staff.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A system of locating a medical imaging device relative to a person support apparatus or a patient, the system comprising:
 a person support apparatus adapted to support a patient;
 a medical imaging device adapted to capture a medical image of the patient on the person support apparatus;
 an optical sensor comprising a camera communicatively coupled to a processor wherein:
  the optical sensor adapted to receive a light signal comprising an image corresponding to the at least one of the person support apparatus, the medical imaging device and the patient,
  the processor adapted to:
   receive a signal corresponding to the light signal from the camera,
   detect one or more objects based on the signal corresponding to the light signal from the camera,
   determine a feature description of the one or more objects to be at least one of the medical imaging device, the person support apparatus and the patient based on a training image, and
   determine a position of the medical imaging device relative to at least one of the person support apparatus and the patient based upon the signal and the feature description of the one or more objects.

2. The system of claim 1 wherein the camera comprises a light detector and the light signal comprises a reflected light signal.

3. The system of claim 2 wherein the reflected light signal is reflected from an optical marker disposed on one of the group comprising: the person support apparatus, the medical imaging device, the patient, a light, a table, a shelf, a fixture, a wall, a ceiling, a post, a beam and a floor.

4. The system of claim 3 wherein the optical marker comprises a retroreflective optical marker.

5. The system of claim 1 wherein the light signal comprises a light signal generated by an active optical marker.

6. The system of claim 5 wherein the active optical marker is disposed on one or more of the group comprising: the person support apparatus, the medical imaging device, the patient, a light, a table, a shelf, a fixture, a wall, a ceiling, a post, a beam and a floor.

7. The system of claim 1 wherein the optical sensor comprises a data storage element adapted to store the determined position.

8. The system of claim 7 wherein the processor is further adapted to compare the stored position to a subsequent determined position.

9. The system of claim 1 wherein the medical imaging device comprises one or more of the group comprising: a radiographic imaging device, a fluoroscopy imaging device, a mammography imaging device, a computed tomography imaging device and a magnetic resonance imaging device.

10. The system of claim 1, wherein the processor detects the one or more objects and determines the feature description of the one or more objects using a scale-invariant feature transform algorithm.

11. A process of locating a medical imaging device relative to a person support apparatus or a patient, the process comprising:
 capturing a light signal with an optical sensor comprising a camera, the light signal comprising an image corresponding to at least one of a patient, a person support apparatus adapted to support the patient and a medical imaging device;
 receiving an electrical signal from the camera corresponding to the light signal at a processor of the optical sensor;
 detecting one or more objects based on the electrical signal from the camera corresponding to the light signal at the processor of the optical sensor;
 determining a feature description of the one or more objects to be at least one of the medical imaging device, the person support apparatus and the patient based on a training image using the processor; and
 determining a relative location of the medical imaging device relative to at least one of the person support apparatus and the patient based on the electrical signal and the feature description of the one or more objects using the processor.

12. The process of claim 11 further comprising storing the relative location in a data storage element.

13. The process of claim 12 further comprising receiving a second light signal corresponding to at least one of the patient, the person support apparatus and the medical imaging device, receiving a second electrical signal from the camera corresponding to the second light signal at the processor and determining a second relative location of the medical imaging device relative to at least one of the person support apparatus and the patient based on the second electrical signal using the processor.

14. The process of claim 13 further comprising determining an error signal using the processor between the second relative location and the relative location.

15. The process of claim 14 further comprising displaying the error signal on a user display device to guide movement of at least one of the medical imaging device, the person support apparatus and the patient.

16. The process of claim 11 wherein the light sensor comprises a light detector and the light signal comprises a reflected light signal.

17. The process of claim 16 wherein the reflected light signal is reflected from an optical marker disposed on one of the group comprising: the person support apparatus, the medical imaging device, the patient, a light, a table, a shelf, a fixture, a wall, a ceiling, a post, a beam and a floor.

18. The process of claim 17 wherein the optical marker comprises a retroreflective optical marker.

19. The process of claim 11 wherein the light signal comprises a light signal generated by an active optical marker.

20. The process of claim 19 wherein the active optical marker is disposed on one or more of the group comprising: the person support apparatus, the medical imaging device and the patient.

21. The process of claim 11 wherein the optical sensor comprises a data storage element adapted to store the determined position.

22. The process of claim 21 wherein the processor is further adapted to compare the stored position to a subsequent determined position.

23. The process of claim 11 wherein the medical imaging device comprises one or more of the group comprising: a radiographic imaging device, a fluoroscopy imaging device, a mammography imaging device, a computed tomography imaging device and a magnetic resonance imaging device.

24. The process of claim 11 wherein the optical sensor comprises a camera-based motion capture system.

25. The process of claim 11 wherein the optical sensor is disposed on one of group comprising: the person support apparatus, the medical imaging device, the patient, a light, a table, a shelf, a fixture, a wall, a ceiling, a post, a beam and a floor.

26. The process of claim 11, wherein the processor is adapted to use a scale-invariant feature transform algorithm when detecting the one or more objects and determining the feature description of the one or more objects.

* * * * *